(12) United States Patent
Schafer et al.

(10) Patent No.: US 10,018,637 B2
(45) Date of Patent: Jul. 10, 2018

(54) METHODS FOR TREATING INFLAMMATORY AND OTHER DISEASES AND THE USE OF BIOMARKERS AS PREDICTORS OF CLINICAL SENSITIVITY TO TREATMENT WITH APREMILAST

(71) Applicant: CELGENE INTERNATIONAL II SARL, Couvet (CH)

(72) Inventors: Peter H. Schafer, Belle Mead, NJ (US); Matthew William Burnell Trotter, Sevilla (ES)

(73) Assignee: CELGENE INTERNATIONAL II SARL (CH)

( * ) Notice: Subject to any disclaimer, the term of this patent is extended or adjusted under 35 U.S.C. 154(b) by 0 days.

(21) Appl. No.: 15/286,302

(22) Filed: Oct. 5, 2016

(65) Prior Publication Data

US 2017/0097360 A1    Apr. 6, 2017

Related U.S. Application Data

(63) Continuation of application No. 62/237,901, filed on Oct. 6, 2015.

(51) Int. Cl.
*G01N 33/68* (2006.01)
*A61K 31/4035* (2006.01)

(52) U.S. Cl.
CPC ..... *G01N 33/6863* (2013.01); *A61K 31/4035* (2013.01); *G01N 2333/523* (2013.01); *G01N 2800/105* (2013.01); *G01N 2800/52* (2013.01); *G01N 2800/60* (2013.01)

(58) Field of Classification Search
CPC ......... G01N 33/6863; G01N 2333/523; G01N 2800/105; G01N 2800/52; G01N 2800/60; A61K 31/4035
USPC ....................................................... 514/341
See application file for complete search history.

(56) References Cited

U.S. PATENT DOCUMENTS

2013/0040835 A1    2/2013    Harris

FOREIGN PATENT DOCUMENTS

| WO | WO 2010077722 A1 | 7/2010 |
| WO | WO 2011117366 A2 | 9/2011 |
| WO | WO 2011117366 A3 | 9/2011 |
| WO | WO 2017060353 A1 | 4/2017 |

OTHER PUBLICATIONS

International Search Reprot and Written Opinion of corresponding PCT Application No. PCT/EP2016/073880 (11 pages), 2016.
Schafer et al., "The pharmacodynamic impact of apremilast, an oral phosphodiesterase 4 inhibitor, on circulating levels of inflammatory biomarkers in patients with psoriatic arthritis: substudy results from a phase III, randomized, placebo-controlled trial (PALACE 1)", J Immunol Res., 2015:906349 (2015).

*Primary Examiner* — Kristin A Vajda
(74) *Attorney, Agent, or Firm* — Jones Day

(57) ABSTRACT

Provided herein are methods for predicting the clinical sensitivity of an inflammatory disease (e.g., ankylosing spondylitis) and a subject's response to treatment with apremilast using the level of a biomarker (e.g., MCP1). Also provided herein are methods for treating an inflammatory disease.

19 Claims, 15 Drawing Sheets

Figure 1A:
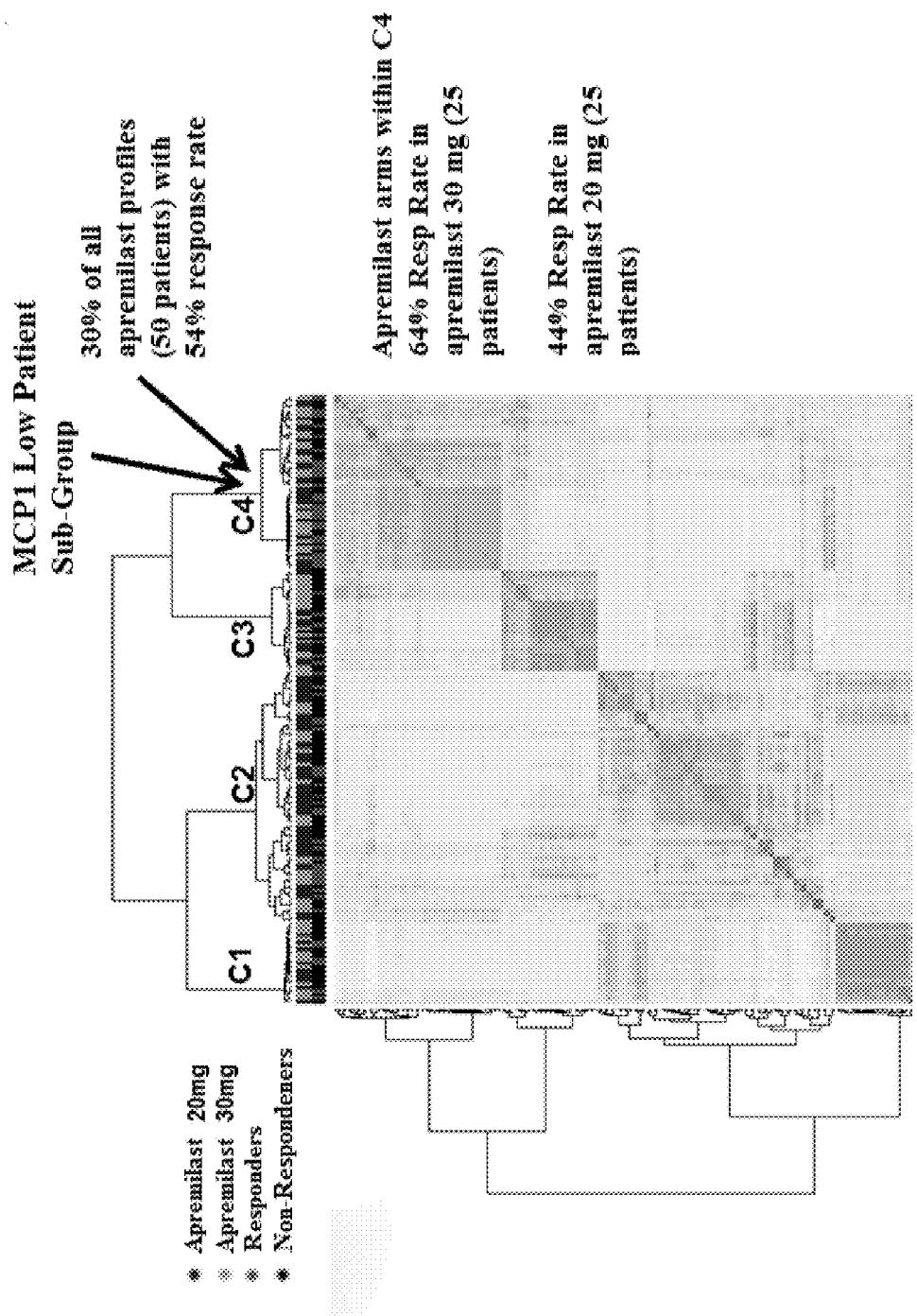

METHODS FOR TREATING INFLAMMATORY AND OTHER DISEASES AND THE USE OF BIOMARKERS AS PREDICTORS OF CLINICAL SENSITIVITY TO TREATMENT WITH APREMILAST

CROSS-REFERENCES TO RELATED APPLICATIONS

This application claims the benefit of priority to U.S. Ser. No. 62/237,901 filed Oct. 6, 2015, which is herein incorporated by reference in its entirety.

1. BACKGROUND

Inflammatory diseases, such as arthritis or related arthritic conditions (e.g., ankylosing spondylitis, osteoarthritis and rheumatoid arthritis), Behcet's disease, inflammatory bowel disease (e.g., Crohn's disease and ulcerative colitis), psoriasis, atopic dermatitis and contact dermatitis are prevalent and problematic ailments. TNF-α plays a central role in the inflammatory response and the administration of their antagonists block chronic and acute responses in animal models of inflammatory disease. Enhanced or unregulated TNF-α production has been implicated in a number of diseases, for example ankylosing spondylitis, Behcet's disease, rheumatoid arthritis, Crohn's disease, and ulcerative colitis.

Phosphodiesterase type 4 (PDE4) belongs to a family of isoenzymes referred to as cyclic nucleotide phosphodiesterases (PDE). It is believed that the primary cellular mechanism for the inactivation of cAMP is the breakdown of adenosine 3',5'-cyclic monophosphate (cAMP) by PDE. Inhibition of PDE4 has been shown to be particularly effective in the inhibition of inflammatory mediator releases.

No treatment for a diagnosed disease is 100% effective in all patient populations having the disease. For example, in the largest study trial, etanercept produced a response rate of 57% compared with 22% for placebo after 24 weeks (response was determined via the validated ASAS 20 response criteria developed by the Assessments in Ankylosing Spondylitis [ASAS] Working Group). See McCormack et al., *BioDrugs: clinical immunotherapeutics, biopharmaceuticals and gene therapy* 18 (3): 199-205 (2003). Accordingly, there is still a significant need for accurate and sensitive methods of identifying patients with various inflammatory diseases or disorders that are likely to be responsive to a treatment.

2. SUMMARY

Provided herein are methods of identifying a subject having a disease or disorder, e.g., ankylosing spondylitis, who is likely to be responsive to a treatment with apremilast, or predicting the responsiveness of a subject having or suspected of having a disease or disorder, e.g., ankylosing spondylitis, to a treatment with apremilast. Also provided herein are methods for treating a patient who is likely to be responsive to apremilast.

In one aspect, provided herein are methods of identifying a subject having ankylosing spondylitis who is likely to be responsive to a treatment with apremilast, or predicting the responsiveness of a subject having or suspected of having ankylosing spondylitis to a treatment with apremilast, comprising:

(a) obtaining a sample from the subject;
(b) measuring the level of monocyte chemotactic protein 1 (MCP1) in the sample; and
(c) diagnosing the subject as being likely to be responsive to apremilast if the level of MCP1 in the sample is lower than a threshold level of MCP1.

In some embodiments, the methods provided herein further comprises administering a therapeutically effective amount of apremilast to the subject diagnosed as being likely to be responsive to apremilast.

In another aspect, provided herein are methods of treating a subject having ankylosing spondylitis, comprising:

(a) identifying the subject having ankylosing spondylitis that may be responsive to a treatment with apremilast, comprising:
   (i) obtaining a sample from the subject;
   (ii) measuring the level of MCP1 in the sample; and
   (iii) diagnosing the subject as being likely to be responsive to apremilast if the level of MCP1 in the sample is lower than a threshold level of MCP 1, and
(b) administering the subject a therapeutically effective amount of apremilast if the subject is identified as being likely to be responsive to treatment with apremilast.

In some embodiments, the threshold level of MCP1 is determined based on the levels of MCP1 in a population. In some embodiments, the threshold level of MCP1 is between 200 pg/ml to 50 pg/ml. In some embodiments, the threshold level of MCP1 is between 105 pg/ml to 70 pg/ml. In some embodiments, the threshold level of MCP1 is lower than 200 pg/ml, 150 pg/ml, 120 pg/ml, 105 pg/ml, 100 pg/ml, 95 pg/ml, 90 pg/ml, 85 pg/ml, 80 pg/ml, 75 pg/ml, or 70 pg/ml. In some embodiments, the threshold level of MCP1 is about 105 pg/ml. In some embodiments, the threshold level of MCP1 is about 95 pg/ml. In some embodiments, the threshold level of MCP1 is about 75 pg/ml.

In some embodiments, the subject is diagnosed as having more than a 50% to 90% likelihood of being responsive to apremilast if the level of MCP1 is lower than the threshold level of MCP1. In other embodiments, the subject is diagnosed as having more than a 50% likelihood of being responsive to apremilast if the level of MCP1 is lower than the threshold level of MCP1. In yet other embodiments, the subject is diagnosed as having more than a 60% likelihood of being responsive to apremilast if the level of MCP1 is lower than the threshold level of MCP1. In yet other embodiments, the subject is diagnosed as having more than a 70% likelihood of being responsive to apremilast if the level of MCP1 is lower than the threshold level of MCP1. In yet other embodiments, the subject is diagnosed as having more than a 80% likelihood of being responsive to apremilast if the level of MCP1 is lower than the threshold level of MCP1. In yet other embodiments, the subject is diagnosed as having more than a 90% likelihood of being responsive to apremilast if the level of MCP1 is lower than the threshold level of MCP1.

3. BRIEF DESCRIPTION OF THE FIGURES

Figure 1B:
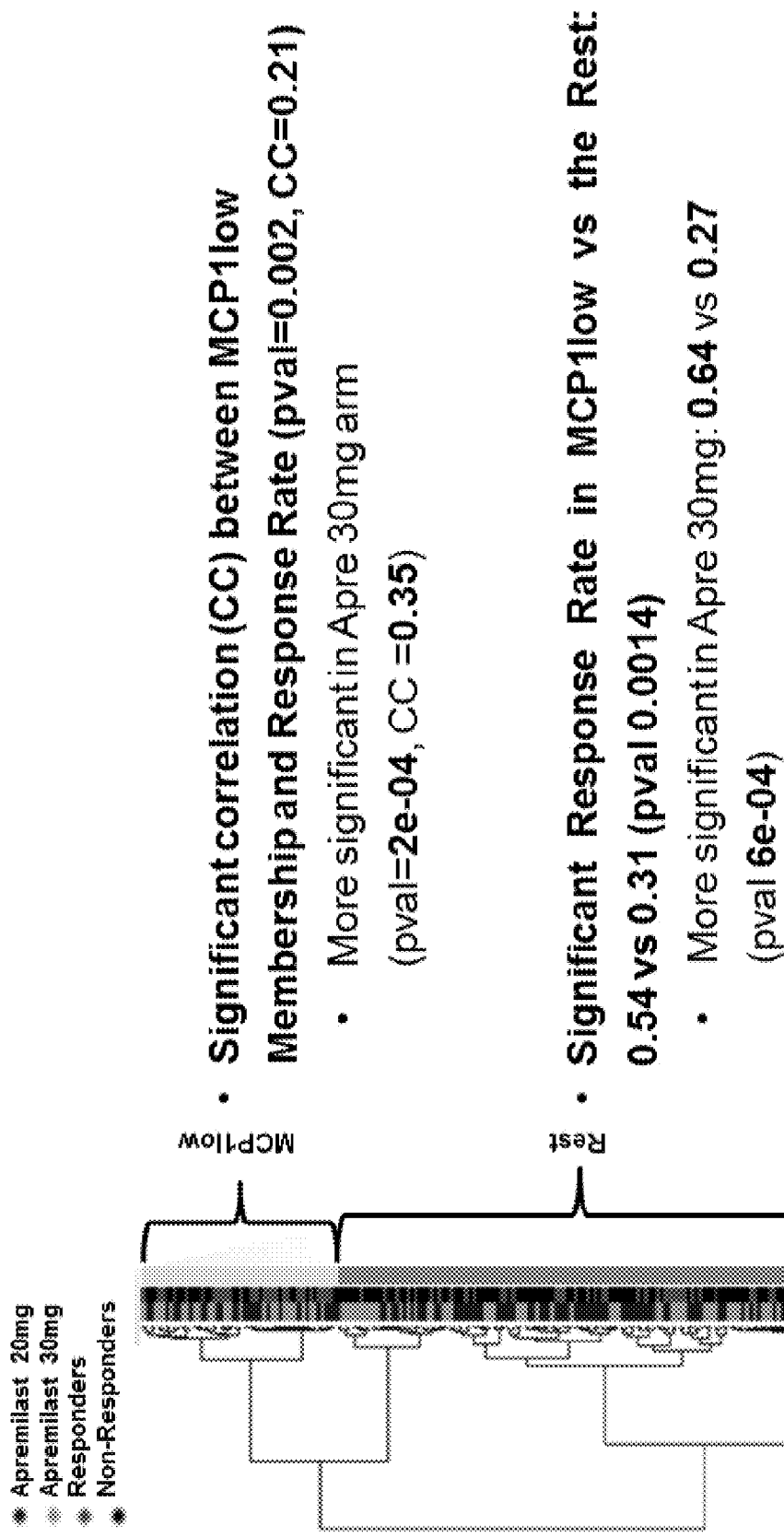
Figure 1C:
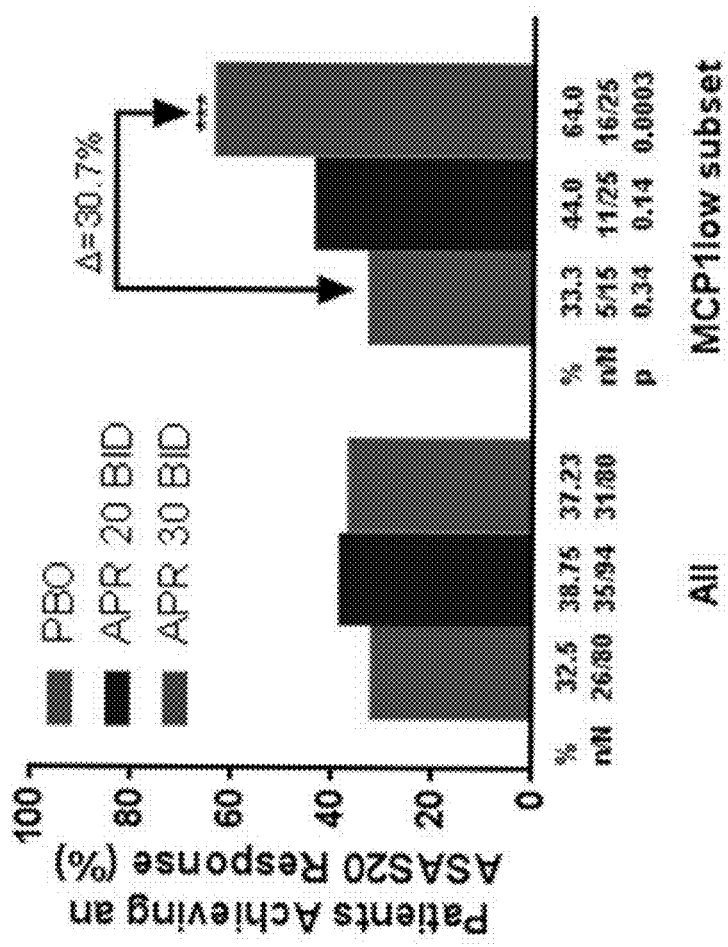
Figure 1D:
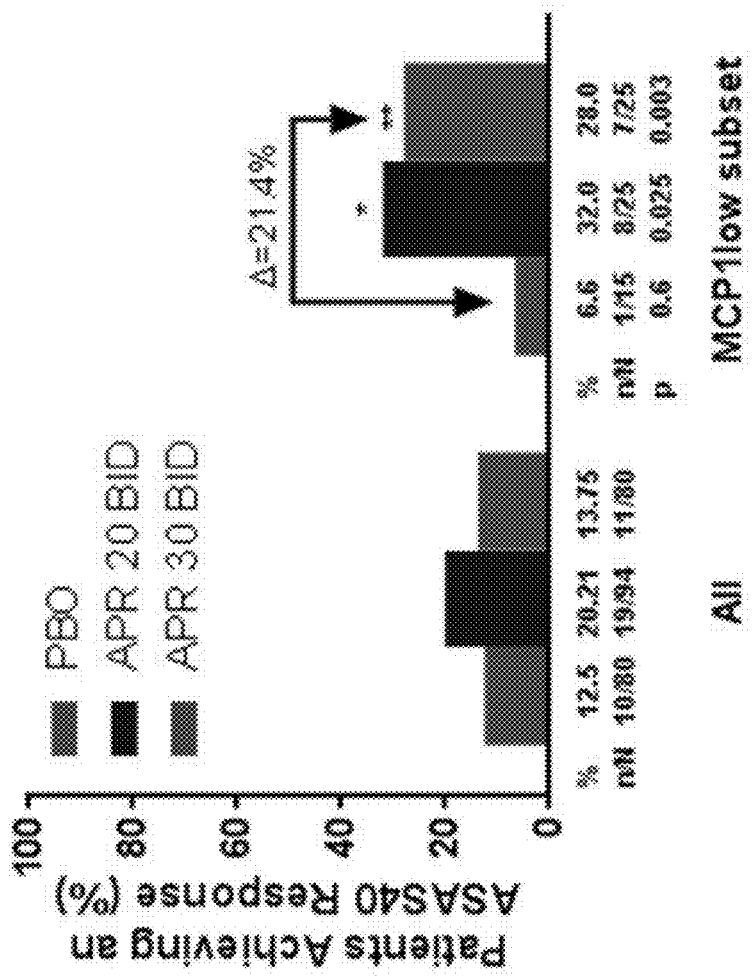

FIGS. 1A-1D show that a patient group (cluster 4 or MCP1 low group) identified based on biomarker expression profile is associated with responsiveness to a treatment with apremilast. FIG. 1A shows unsupervised clustering results with biomarker profiles and identification of a group of patients (cluster 4) with higher response rate to apremilast treatment. FIG. 1B shows cluster 4 is significantly associated with responsiveness to apremilast. FIG. 1C shows the response rate to apremilast treatment is significantly higher in the MCP1 low patient group in the ASAS20 study. FIG. 1D shows the response rate to apremilast treatment is significantly higher in the MCP1 low patient group in the ASAS40 study.

Figure 2A:
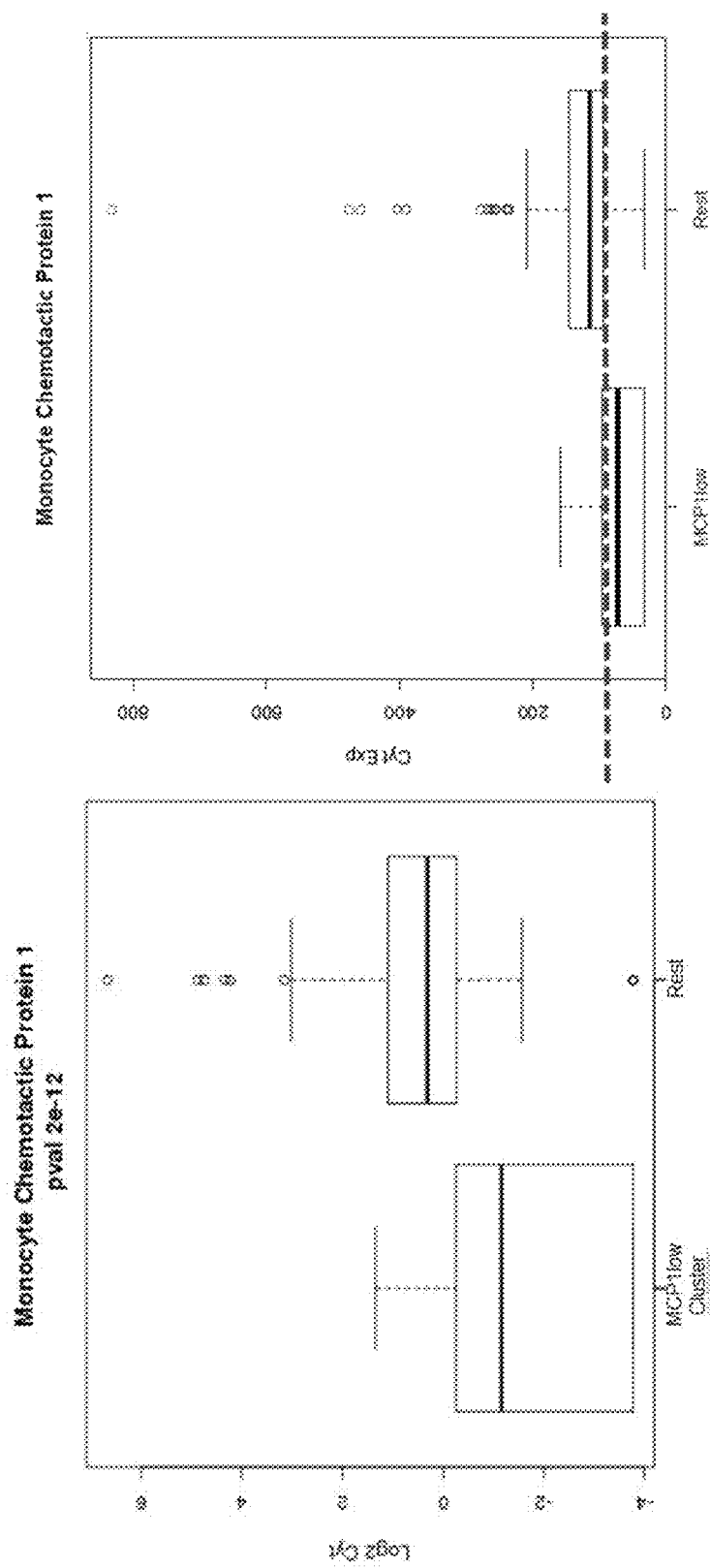
Figure 2B:
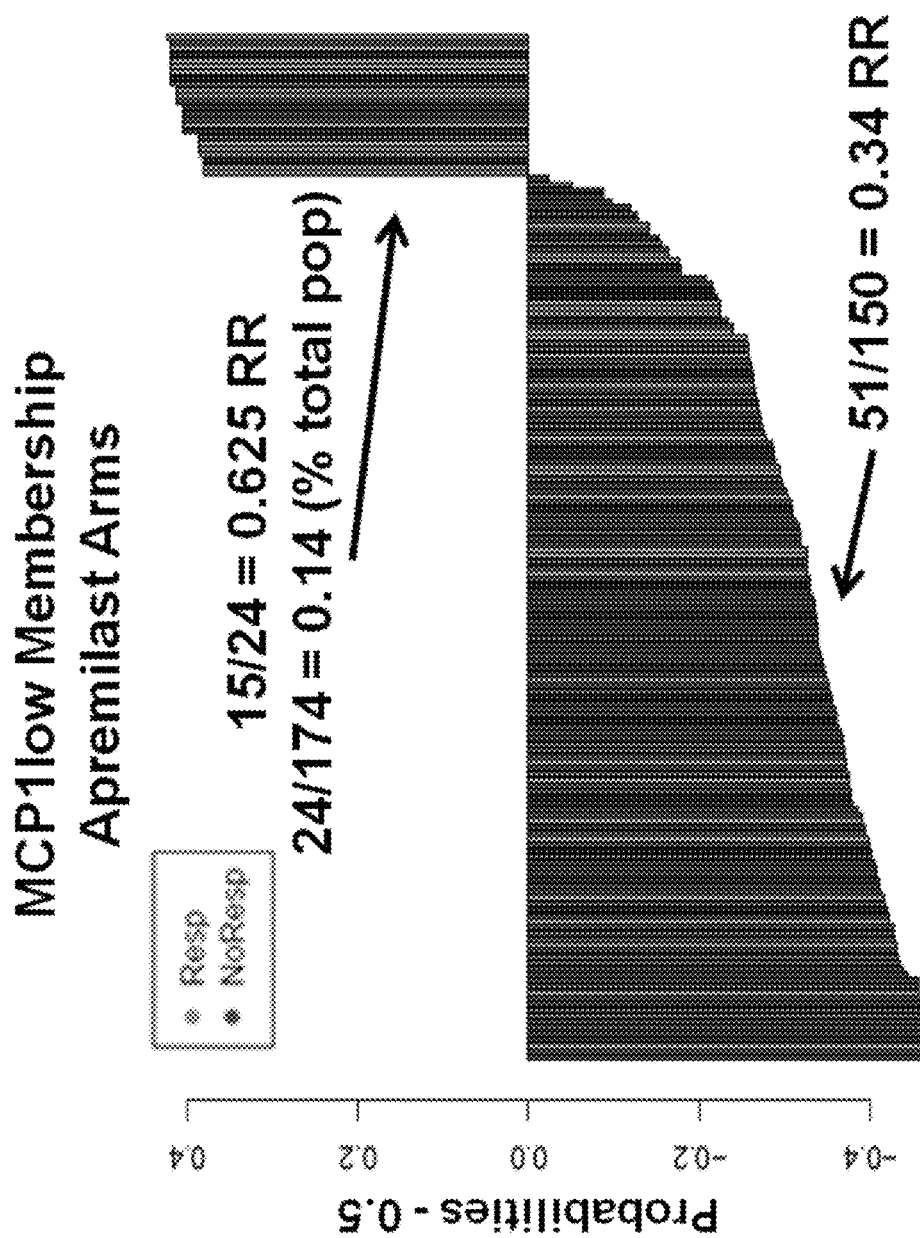
Figure 2C:
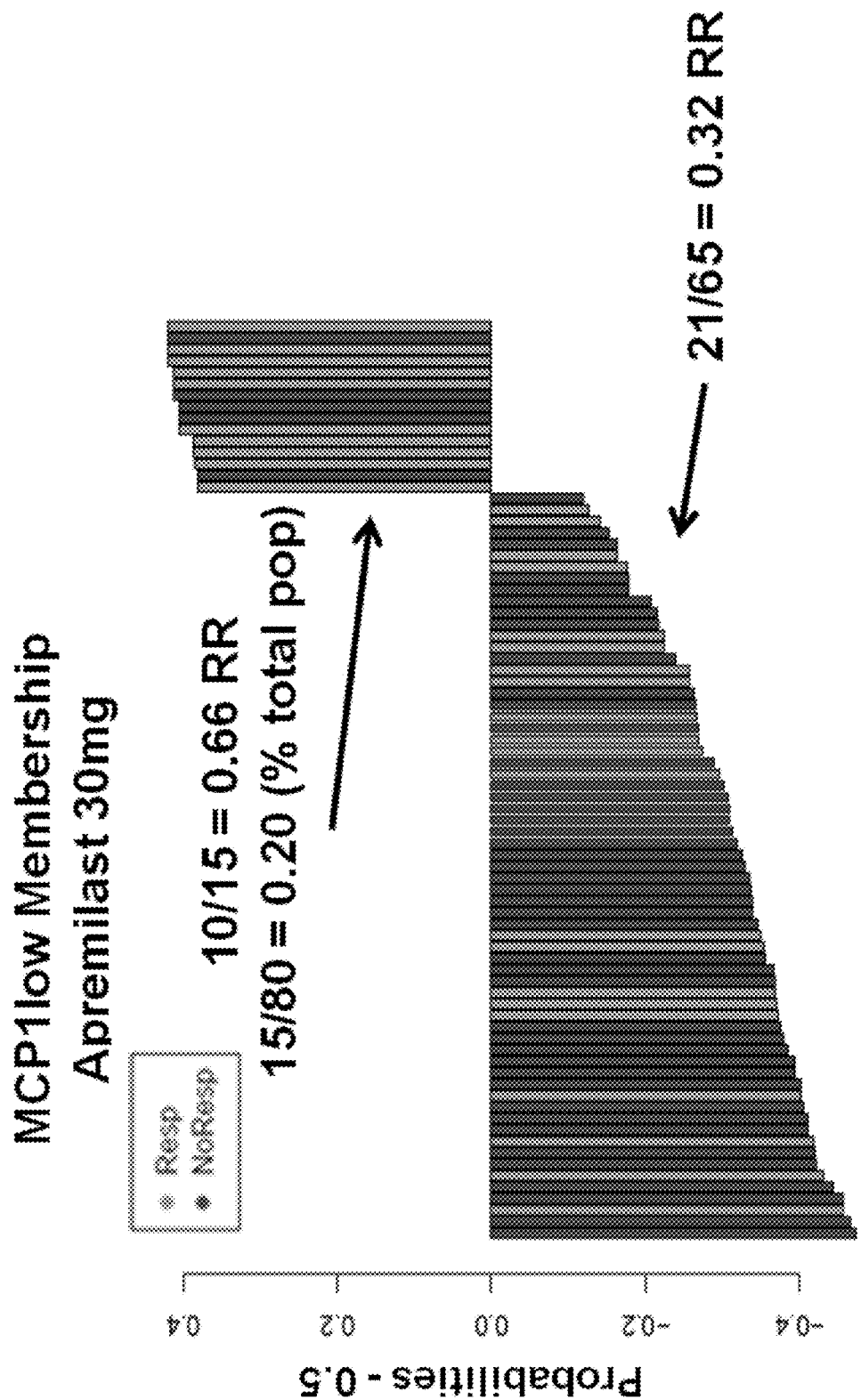
Figure 2D:
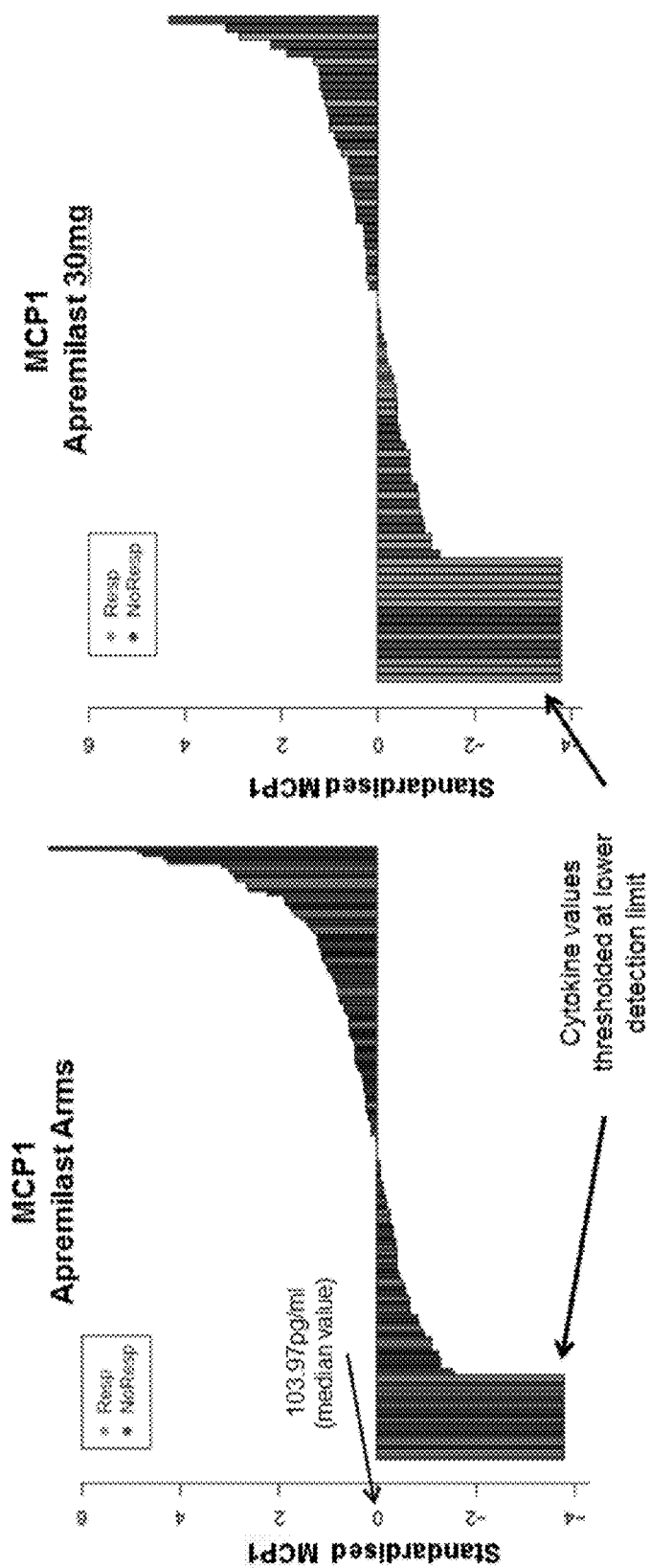
Figure 2E:
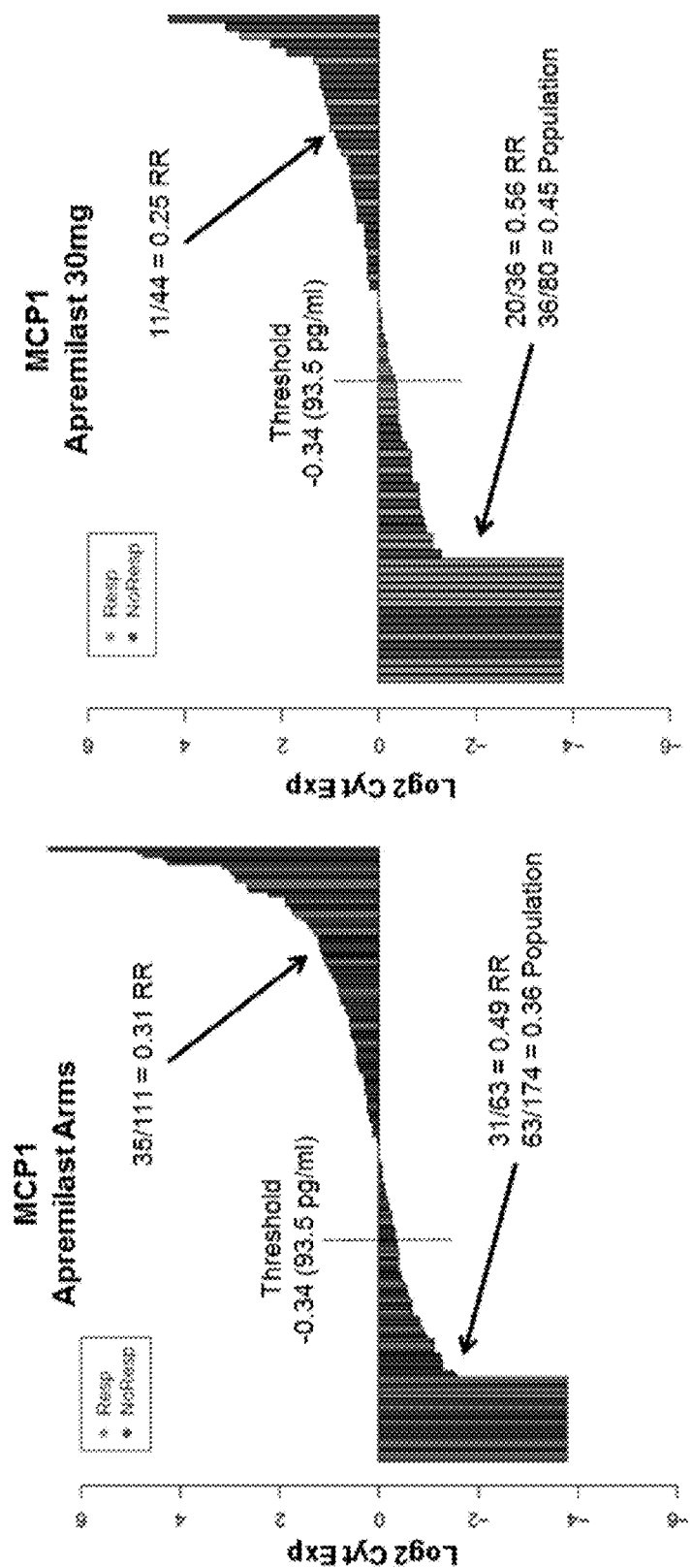
Figure 2F:
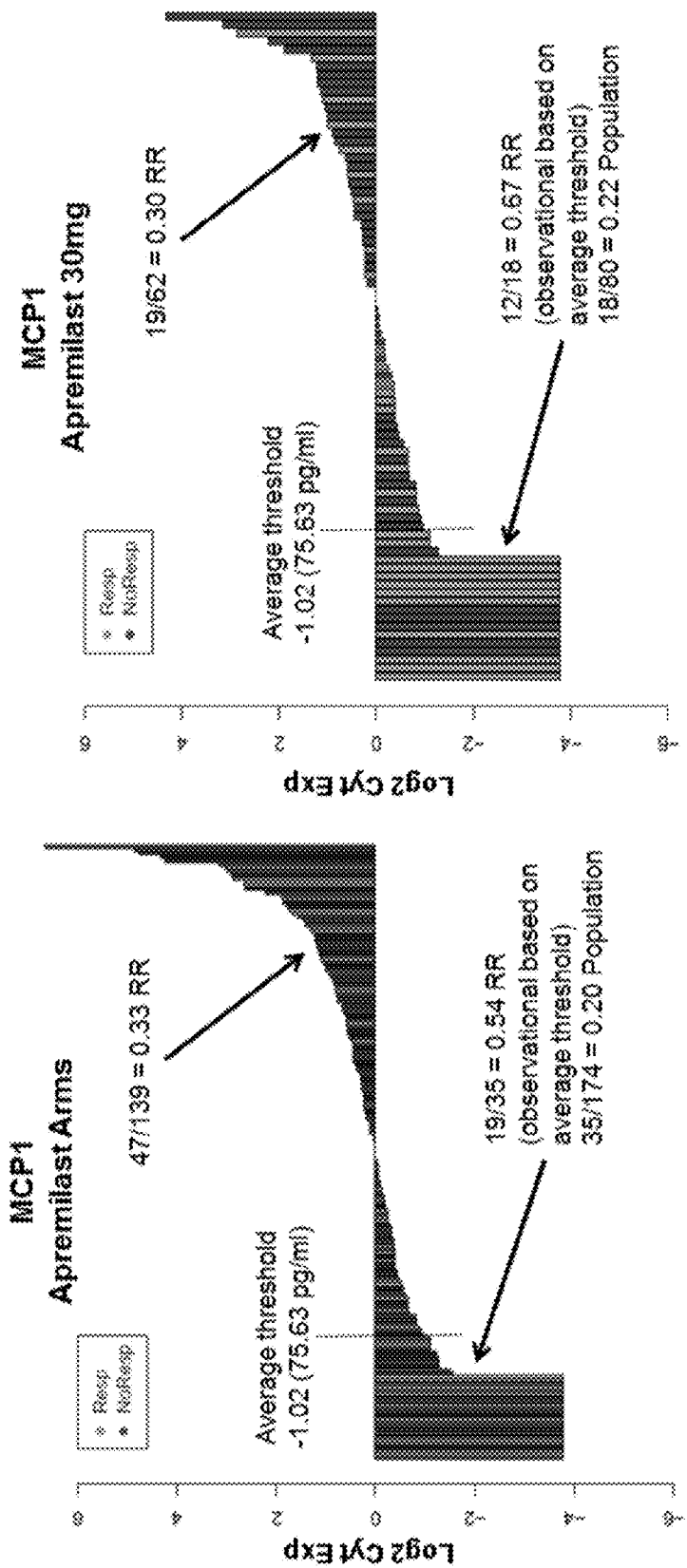

FIGS. 2A-2F shows using MCP1 level alone to classify a patient for the purpose of predicting the patient's response to a treatment with apremilast. FIG. 2A shows that the patients in the cluster 4 patient group have significantly lower expression level of MCP1 as compared with the rest patients. FIG. 2B shows the level of MCP1 was used to differentiate a patient subgroup (14% of total population) highly responsive to apremilast (in apremilast arm with either 20 mg or 30 mg apremilast) with a response rate of about 62.5%. FIG. 2C shows MCP1 level differentiated a patient subgroup (20% of the apremilast 30 mg arm) with a response rate to 30 mg apremilast treatment of about 66.6%. FIG. 2D shows MCP1 distribution using a threshold level (103.97 pg/ml) calculated based on the median value of MCP1 of the total population. FIG. 2E shows MCP1 distribution using the threshold calculated as the mid-point between MCP1 low median and non-MCP1 low median across all patients. FIG. 2F shows MCP1 distribution using the threshold level calculated as the mean of the thresholds obtained from 10-fold cross validation.

Figure 3A:
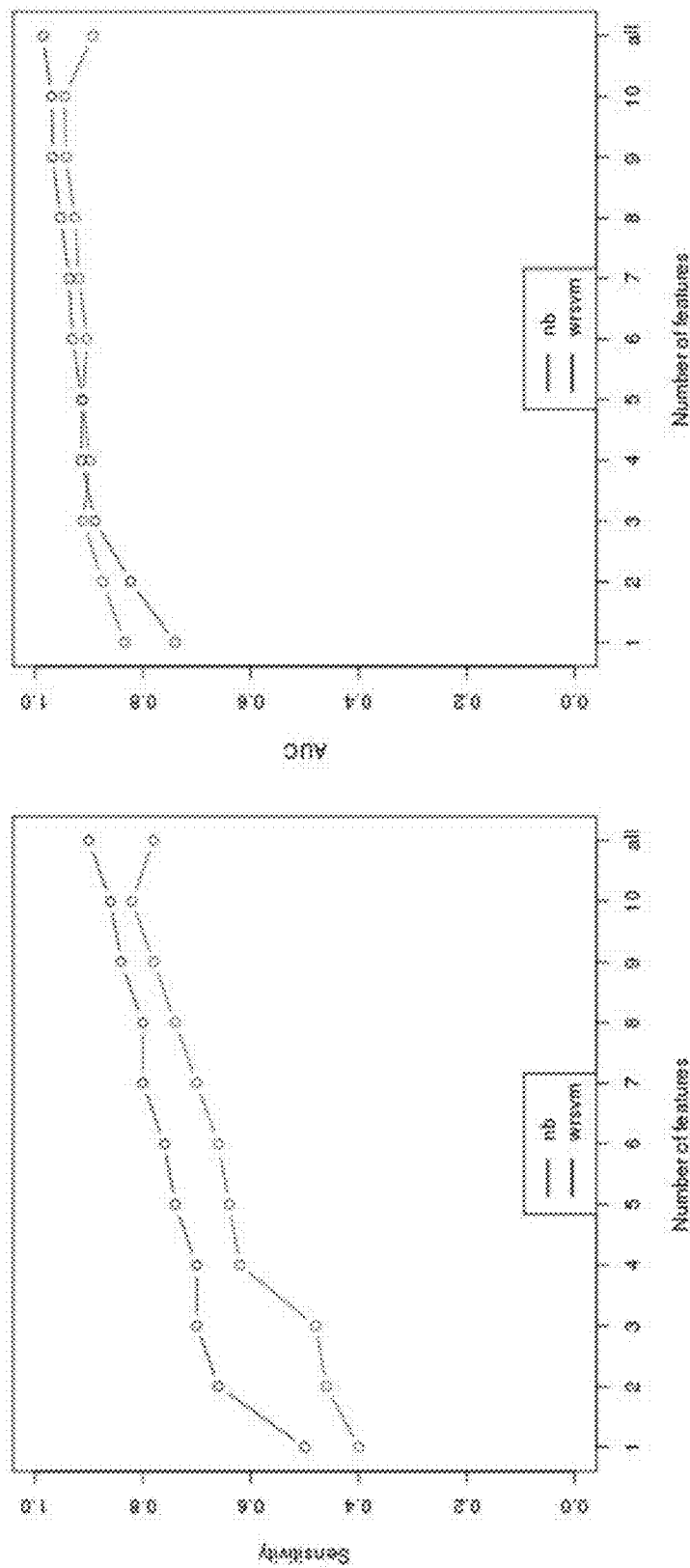
Figure 3B:
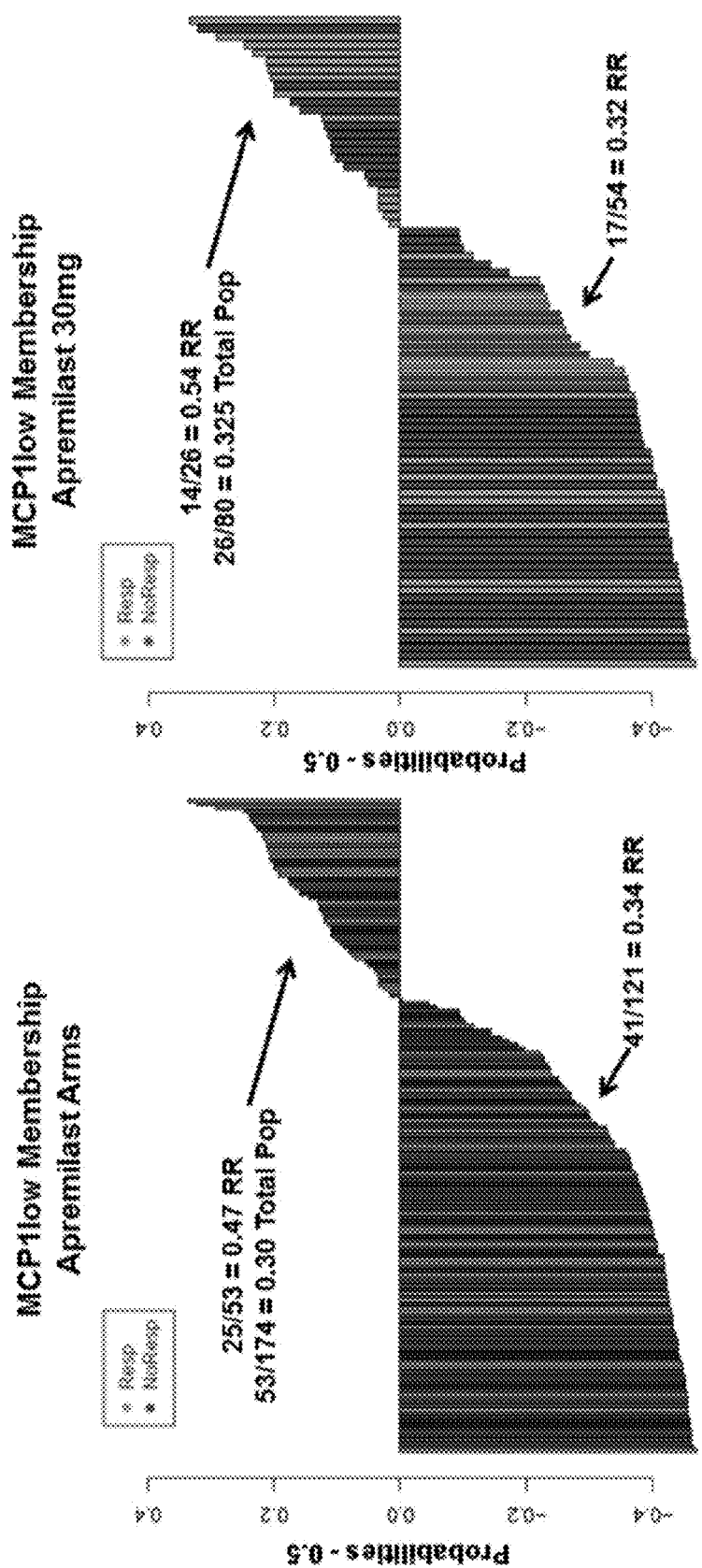
Figure 3C:
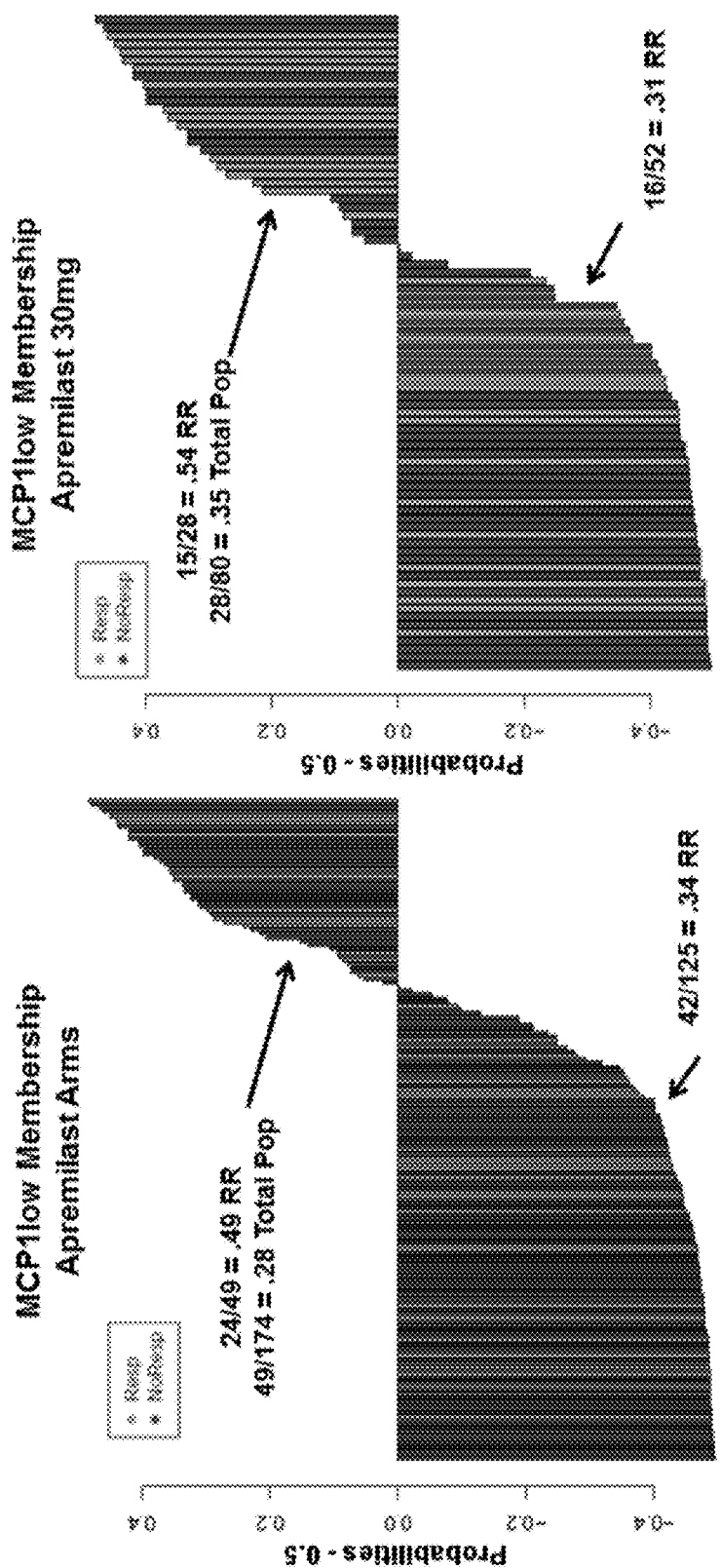
Figure 3D:
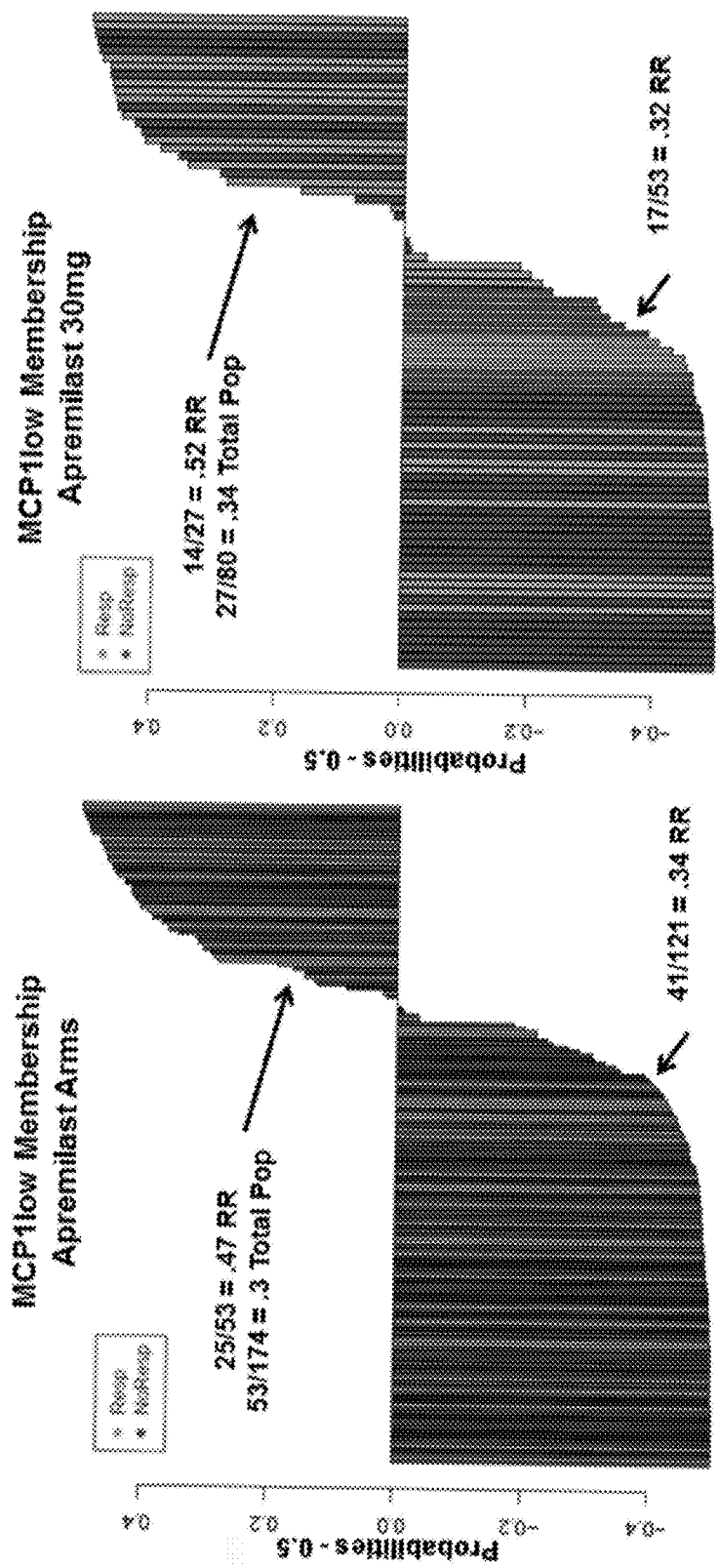
Figure 3E:
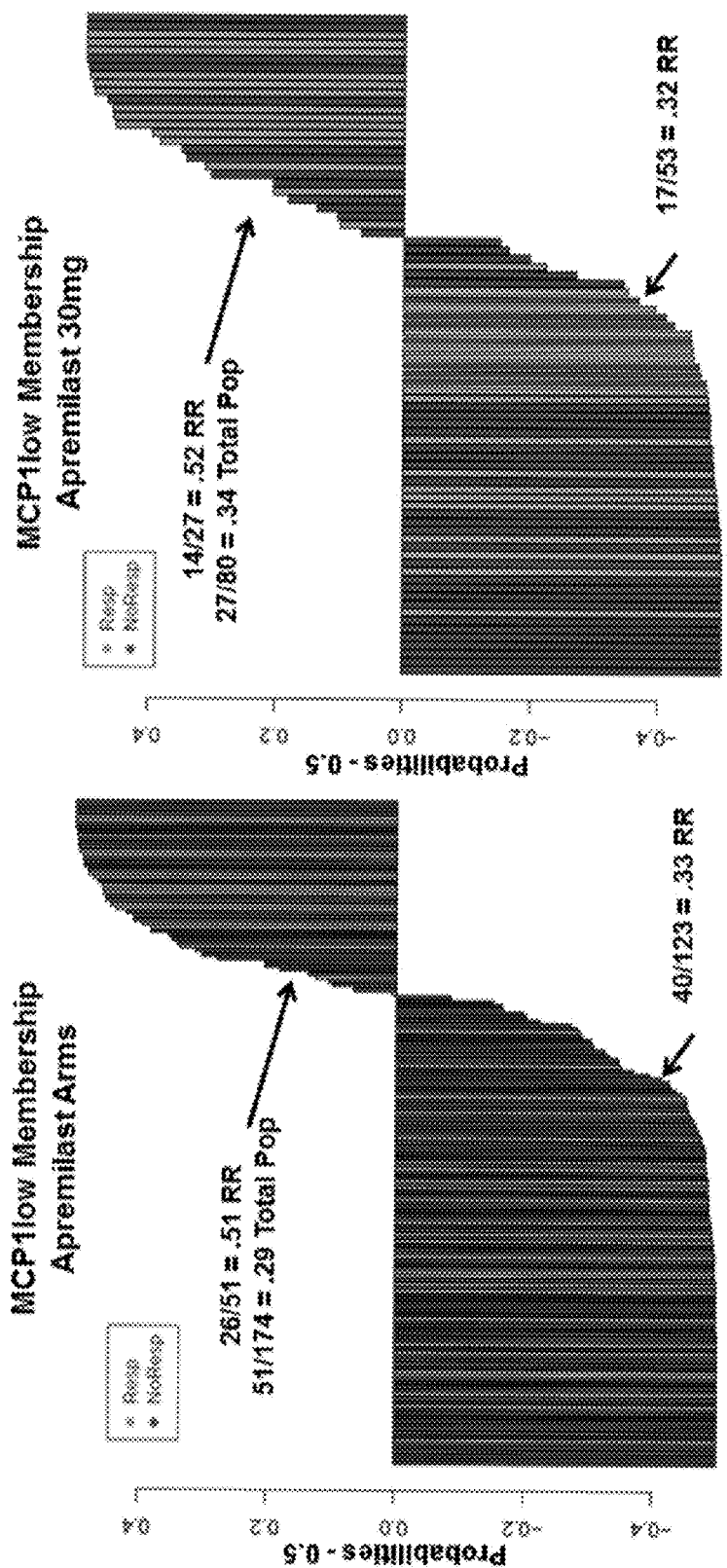

FIGS. 3A-3E show using expression levels of multiple biomarkers for classifying a patient for the purpose of predicting the patient's response to a treatment with apremilast. FIG. 3A shows sensitivity and AUC of two classifiers—Naive Bayes and Weighted RSVM. FIG. 3B shows a patient distribution plot based on the expression levels of the top 2 biomarkers (MCP1 and Interleukin-15) identified in the present study. FIG. 3C shows a patient distribution plot based on the expression levels of the top 5 biomarkers (MCP1, Interleukin-15, C—reactive protein, Matrix Metalloproteinase-3, and Interleukin-1 receptor antagonist) identified in the present study. FIG. 3D shows a patient distribution plot based on the expression levels of the top 10 biomarkers (MCP1, Interleukin-15, C-Reactive Protein, Matrix Metalloproteinase-3, Interleukin-1 receptor antagonist, von Willebrand Factor, Eotaxin-1, Alpha-1-Antitrypsin, Macrophage Inflammatory Protein-1 beta, and Vascular Cell Adhesion Molecule-1) identified in the present study. FIG. 3E shows a patient distribution plot based on the expression levels of all of the 49 biomarkers provided in the present study.

4. DETAILED DESCRIPTION

4.1 Definitions

As used herein, the term "apremilast" refers to (+)-2-[1-(3-ethoxy-4-methoxyphenyl)-2-methylsulfonylethyl]-4-acetylaminoisoindoline-1,3-dione (also known as N-[2-[(1S)-1-(3-ethoxy-4-methoxylphenyl)-2-(methylsulfonyl)ethyl]-2,3-dihydro-1,3-dioxo-1H-isoindol-4-yl]acetamide), or a pharmaceutically acceptable salt, solvate, hydrate, co-crystal, clathrate, a polymorph, stereoisomer, or isotopologue thereof. The active enantiomer of apremilast is believed to be the (+) enantiomer. The structure of (+)-2-[1-(3-ethoxy-4-methoxyphenyl)-2-methylsulfonylethyl]-4-acetylaminoisoindoline-1,3-dione, also known as N-[2-[(1S)-1-(3-ethoxy-4-methoxylphenyl)-2-(methylsulfonyl)ethyl]-2,3-dihydro-1,3-dioxo-1H-isoindol-4-yl]acetamide is:

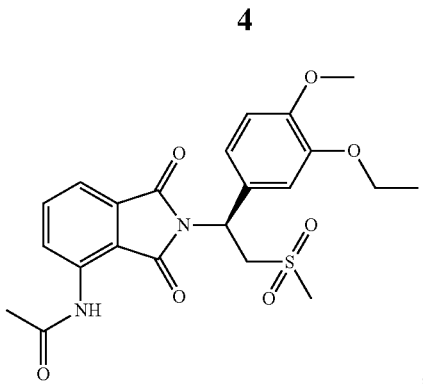

which may be prepared according to methods disclosed in U.S. Pat. Nos. 6,962,940; 7,208,516; 7,427,638; or 7,893,101, each of which is incorporated herein by reference in its entirety.

As used herein, the terms "compound" and "treatment compound" are used interchangeably, and include apremilast.

As used herein and unless otherwise indicated, the term "pharmaceutically acceptable salt" includes, but is not limited to, salts prepared from pharmaceutically acceptable non-toxic acids or bases including inorganic acids and bases and organic acids and bases. Suitable pharmaceutically acceptable base addition salts provided herein include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids, such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts.

As used herein and unless otherwise indicated, the term "hydrate" means a compound provided herein or a salt thereof that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., monohydrate, dihydrate, trihydrate, tetrahydrate and the like).

As used herein and unless otherwise indicated, the term "polymorph" means solid crystalline forms of a compound provided herein or complex thereof. Different polymorphs of the same compound can exhibit different physical, chemical and/or spectroscopic properties.

As used herein and unless otherwise specified, the term "prodrug" means a derivative of a compound that can hydrolyze, oxidize, or otherwise react under biological conditions (in vitro or in vivo) to provide the compound. Examples of prodrugs include, but are not limited to, derivatives and metabolites of apremilast that include biohydrolyzable moieties, such as biohydrolyzable amides, biohydrolyzable esters, biohydrolyzable carbamates, biohydrolyzable carbonates, biohydrolyzable ureides, and biohydrolyzable phosphate analogues.

As used herein, and unless otherwise specified, the term "enantiomer," "isomer" or "stereoisomer" encompasses all enantiomerically/stereomerically pure and enantiomerically/stereomerically enriched compounds provided herein.

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure, when the compound contains greater than or equal to 80%, 90%, 95%, 96%, 97%, 98% or 99% of one stereoisomer, and 20%, 10%, 5%, 4%, 3%, 2%, 1% or less of the counter stereoisomer. "Substantially free of its (R) enantiomer" is encompassed by the term stereomerically pure or enantiomerically pure.

It should also be noted compounds can contain unnatural proportions of atomic isotopes at one or more of the atoms. For example, the compounds may be radiolabeled with radioactive isotopes, such as for example tritium ($^3H$), iodine-125 ($^{125}I$), sulfur-35 ($^{35}S$), or carbon-14 , ($^{14}C$), or may be isotopically enriched, such as with deuterium ($^2H$), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds, for example, the isotopologues are deuterium, carbon-13, or nitrogen-15 enriched compounds.

As used herein, and unless otherwise specified, the terms "treat," "treating" and "treatment" contemplate an action that occurs while a patient is suffering from the specified disease or disorder, which reduces the severity or symptoms of the disease or disorder, or retards or slows the progression or symptoms of the disease or disorder.

As used herein, unless otherwise specified, the terms "prevent," "preventing" and "prevention" contemplate an action that occurs before a patient begins to suffer from the specified disease or disorder, which inhibits or reduces the severity or symptoms of the disease or disorder.

As used herein, and unless otherwise indicated, the terms "manage," "managing," and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

As used herein, and unless otherwise specified, the term "therapeutically effective amount" of a compound is an amount sufficient to provide a therapeutic benefit in the treatment or management of a disease or disorder, or to delay or minimize one or more symptoms associated with the presence of the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of a disease or disorder, or enhances the therapeutic efficacy of another therapeutic agent. The term also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "responsiveness" or "responsive" when used in reference to a treatment refer to the degree of effectiveness of the treatment in lessening or decreasing the symptoms of a disease being treated. For example, the term "increased responsiveness" when used in reference to a treatment of a cell or a subject refers to an increase in the effectiveness in lessening or decreasing the symptoms of the disease when measured using any methods known in the art. In certain embodiments, the increase in the effectiveness is at least about 5%, at least about 10%, at least about 20%, at least about 30%, at least about 40%, or at least about 50%. An improvement in the disease or disorder can be characterized as a complete or partial response. "Complete response" refers to an absence of clinically detectable disease. "Partial response" refers to at least about a 10%, 20%, 30%, 40%, 50%, 60%, 70%, 80%, or 90% decrease in any symptoms of the disease. The term "treatment" contemplates both a complete and a partial response.

The term "likelihood" or "likely" generally refers to an increase in the probability of an event.

The term "predict" generally means to determine or tell in advance. When used to "predict" the effectiveness of a treatment, for example, the term "predict" can mean that the likelihood of the outcome of the treatment can be determined at the outset, before the treatment has begun, or before the treatment period has progressed substantially.

As used herein the terms "polypeptide" and "protein" as used interchangeably herein, refer to a polymer of amino acids of three or more amino acids in a serial array, linked through peptide bonds. The term "polypeptide" includes proteins, protein fragments, protein analogues, oligopeptides and the like. The term polypeptide as used herein can also refer to a peptide. The amino acids making up the polypeptide may be naturally derived, or may be synthetic. The polypeptide can be purified from a biological sample. The polypeptide, protein, or peptide also encompasses modified polypeptides, proteins, and peptides, e.g., a glycopolypeptide, glycoprotein, or glycopeptide; or a lipopolypeptide, lipoprotein, or lipopeptide.

The term "antibody" is used herein in the broadest sense and covers fully assembled antibodies, antibody fragments which retain the ability to specifically bind to the antigen (e.g., Fab, F(ab')$_2$, Fv, and other fragments), single chain antibodies, diabodies, antibody chimeras, hybrid antibodies, bispecific antibodies, humanized antibodies, and the like. The term "antibody" covers both polyclonal and monoclonal antibodies. The term "antibody" and "immunoglobulin" or "Ig" may be used interchangeably herein. Antibodies provided herein include, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above. In particular, antibodies provided herein include immunoglobulin molecules and immunologically active portions of immunoglobulin molecules, i.e., antigen binding domains or molecules that contain an antigen-binding site that immunospecifically binds to a biomarker provided herein. The antibodies provided herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. In certain embodiments, antibodies provided herein are IgG antibodies, or a class (e.g., human IgG1 or IgG4) or subclass thereof.

The term "expressed" or "expression" as used herein refers to the transcription from a gene to give a ribonucleic acid molecule at least complementary in part to a region of one of the two nucleic acid strands of the gene. The term "expressed" or "expression" as used herein also refers to the translation from the RNA molecule to give a protein, a polypeptide or a portion thereof.

As used herein, the term "level" refers to the amount, accumulation, or rate of a biomarker molecule. A level can be represented, for example, by the amount or the rate of synthesis of a messenger RNA (mRNA) encoded by a gene, the amount or the rate of synthesis of a polypeptide or protein encoded by a gene, or the amount or the rate of synthesis of a biological molecule accumulated in a cell or biological fluid. The term "level" refers to an absolute amount of a molecule in a sample or to a relative amount of the molecule, determined under steady-state or non-steady-state conditions. An mRNA expressed at a higher level can be, for example, present at a level of about 5%, 10%, 20%, 30%, 40%, 50%, 60%, 70%, 90%, 100%, 200%, 300%, 500%, 1,000%, 5,000% or more of the comparative control mRNA level. An mRNA expressed at a lower level can be, for example, present at a level of about 99%, 95%, 90%, 80%, 70%, 60%, 50%, 40%, 30%, 20%, 10%, 1% or less of the comparative control mRNA level. Similarly, a polypeptide or protein biomarker at a higher level can be, for example, present at a level of about 5%, 10%, 20%, 30%, 40%, 50%, 60%, 70%, 90%, 100%, 200%, 300%, 500%, 1,000%, 5,000% or more of the comparative control protein level. A polypeptide or protein biomarker expressed at a lower level can be, for example, present at a level of about 99%, 95%, 90%, 80%, 70%, 60%, 50%, 40%, 30%, 20%, 10%, 1% or less of the comparative control protein level.

The terms "determining", "measuring", "evaluating", "assessing" and "assaying" as used herein generally refer to any form of measurement, and include determining if an element is present or not. These terms include both quantitative and/or qualitative determinations. Assessing may be relative or absolute. "Assessing the presence of" can include determining the amount of something present, as well as determining whether it is present or absent.

The terms "nucleic acid" and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. As used herein in the context of a polynucleotide sequence, the term "bases" (or "base") is synonymous with "nucleotides" (or "nucleotide"), i.e., the monomer subunit of a polynucleotide. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural nucleotides, nucleotide mimetics, such as 2'-modified nucleosides, peptide nucleic acids, oligomeric nucleoside phosphonates, and any polynucleotide that has added substituent groups, such as protecting groups or linking moieties.

As used herein, the term "complementary" refers to specific binding between polynucleotides based on the sequences of the polynucleotides. As used herein, a first polynucleotide and a second polynucleotide are complementary if they bind to each other in a hybridization assay under stringent conditions, e.g. if they produce a given or detectable level of signal in a hybridization assay. Portions of polynucleotides are complementary to each other if they follow conventional base-pairing rules, e.g. A pairs with T (or U) and G pairs with C, although small regions (e.g. less than about 3 bases) of mismatch, insertion, or deleted sequence may be present.

As used herein, the term "sequence identity" or "identity" in the context of two nucleic acid sequences refers to the residues in the two sequences which are the same when aligned for maximum correspondence over a specified comparison window, and can take into consideration additions, deletions and substitutions.

As used herein, the term "substantial identity" or "homologous" in their various grammatical forms in the context of polynucleotide generally means that a polynucleotide comprises a sequence that has a desired identity, for example, at least 60% identity, at least 70% sequence identity, at least 80%, at least 90% or at least 95%, compared to a reference sequence. Another indication that nucleotide sequences are substantially identical is if two molecules hybridize to each other under stringent conditions.

As used herein, the terms "isolated" and "purified" refer to isolation of a substance (such as mRNA, antibody or protein) such that the substance comprises a substantial portion of the sample in which it resides, i.e. greater than the substance is typically found in its natural or un-isolated state. Typically, a substantial portion of the sample comprises, e.g., greater than 1%, greater than 2%, greater than 5%, greater than 10%, greater than 20%, greater than 50%, or more, usually up to about 90%-100% of the sample. For example, a sample of isolated mRNA can typically comprise at least about 1% total mRNA. Techniques for purifying polynucleotides are well known in the art and include, for example, gel electrophoresis, ion-exchange chromatography, affinity chromatography, flow sorting, and sedimentation according to density.

As used herein, the term "capture agent," refers to an agent that binds an mRNA or protein through an interaction that is sufficient to permit the agent to bind and concentrate the mRNA or protein from a homogeneous mixture.

As used herein, the term "probe" refers to a capture agent that is directed to a specific target mRNA biomarker sequence. Accordingly, each probe of a probe set has a respective target mRNA biomarker. A probe/target mRNA duplex is a structure formed by hybridizing a probe to its target mRNA biomarker.

As used herein, the term "nucleic acid probe" or "oligonucleotide probe" refers to a nucleic acid capable of binding to a target nucleic acid of complementary sequence, such as the mRNA biomarkers provided herein, through one or more types of chemical bonds, usually through complementary base pairing, usually through hydrogen bond formation. As used herein, a probe may include natural (e.g., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are can be directly labeled with isotopes, for example, chromophores, lumiphores, chromogens, or indirectly labeled with biotin to which a streptavidin complex may later bind. By assaying for the presence or absence of the probe, one can detect the presence or absence of a target mRNA biomarker of interest.

As used herein, the term "stringent assay conditions" refers to conditions that are compatible to produce binding pairs of nucleic acids, e.g., probes and target mRNAs, of sufficient complementarity to provide for the desired level of specificity in the assay while being generally incompatible to the formation of binding pairs between binding members of insufficient complementarity to provide for the desired specificity. The term stringent assay conditions generally refer to the combination of hybridization and wash conditions.

As used herein, a "label" or a "detectable moiety" in reference to a nucleic acid, refers to a composition that, when linked with a nucleic acid, renders the nucleic acid detectable, for example, by spectroscopic, photochemical, biochemical, immunochemical, or chemical means. Exemplary labels include, but are not limited to, radioactive isotopes, magnetic beads, metallic beads, colloidal particles, fluorescent dyes, enzymes, biotin, digoxigenin, haptens, and the like. A "labeled nucleic acid or oligonucleotide probe" is generally one that is bound, either covalently, through a linker or a chemical bond, or noncovalently, through ionic bonds, van der Waals forces, electrostatic attractions, hydrophobic interactions, or hydrogen bonds, to a label such that the presence of the nucleic acid or probe can be detected by detecting the presence of the label bound to the nucleic acid or probe.

As used herein, the term "sample" relates to a material or mixture of materials, typically, although not necessarily, in fluid form, containing one or more components of interest. "Biological sample" as used herein refers to a sample obtained from a biological subject, including sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, fractions and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like.

As used herein, a "biological marker" or "biomarker" is a substance whose amount or detection indicates a particular biological state. In another embodiment, biomarkers can either be determined individually, or several biomarkers can be measured simultaneously. Exemplary biomarkers of the present application are those described in Section 4.2 below.

As used herein, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, the term "classifier" refers to a mathematical function that separates two or more groups, bodies or distributions of data according to the values with which each example of data is described, or an output of a function applied to those values in a manner that may be used to assign new data examples to one or more of the groups, bodies or distributions separated.

As used herein, the terms "subject" and "patient" refer to an animal including human being.

4.2 Methods of Selecting Patients, Predicting Responsiveness and Treating

The present disclosure is based, in part, on the finding that a group of patients selected based on expression level(s) of one or more biomarker(s) have a higher likelihood to be responsive to a treatment with a PDE4 inhibitor, e.g., apremilast. Thus, provided herein are certain biomarkers (e.g., a cytokine such as MCP1) for selecting patients for a treatment with apremilast or for predicting a patient's response for a treatment with apremilast.

Also provided herein are methods of identifying a subject having a disease or disorder, predicting the responsiveness of a subject having or suspected of having a disease or disorder, treating a subject having or suspected of having a disease or disorder, or correlating the level(s) of one or more biomarker(s) in a sample with a likelihood of the subject being responsive to a treatment with a PDE4 inhibitor.

In certain embodiments, the disease or disorder is selected from the group consisting of psoriasis, psoriatic arthritis, rheumatoid arthritis, rheumatoid spondylitis, osteoarthritis, other arthritic conditions, non-radiographic axial spondyloarthropathy, Crohn's disease, inflammatory bowel disease, ulcerative colitis, celiac disease, atopic dermatitis, and multiple sclerosis. In some embodiments, the disease or disorder is a chronic inflammatory disease. In some embodiments, the inflammatory disease is ankylosing spondylitis.

In one aspect, the level of a single biomarker is used for identifying a subject having a disease or disorder who is likely to be responsive to a treatment with apremilast, or predicting the responsiveness of a subject having or suspected of having a disease or disorder to a treatment with apremilast. In another aspect, the levels of two or more biomarkers are used for identifying a subject having a disease or disorder who is likely to be responsive to a treatment with apremilast, or predicting the responsiveness of a subject having or suspected of having a disease or disorder to a treatment with apremilast.

According to the present disclosure, the level(s) of one or more biomarker(s) can be correlated with a likelihood of a subject being responsive to a treatment with a PDE4 inhibitor. e.g., apremilast. In certain embodiments, correlating involves associating the level(s) of one or more biomarker(s) measured in a subject sample with a likelihood that a patient responds to PDE4 inhibitor treatment, otherwise known as a response rate. For example, a threshold score (e.g., a threshold level for one biomarker, or a threshold composite score for multiple biomarkers) using one or more biomarkers in a population having the disease or disorder is measured or calculated. Based on the threshold score, a sub-group of the patient population is identified (e.g., the sub-group contains only those patients with a threshold score e.g., a threshold level of X). The likelihood that a patient from this sub-group is responsive to PDE4 treatment is calculated (i.e. if the sub-group contains 20 patients, and 15 of those patients responded to treatment, then the sub-group has a 75% response rate). The same one or more biomarkers used to calculate the threshold score (e.g., the threshold level) are measured or calculated in a sample from a patient that is going to be diagnosed or treated. The patient's biomarker level(s) or the calculation result based on which is then compared to the threshold score (e.g., the threshold level of X used in the above example) and correlated with the calculated response rate of the sub-group depending on if the patient's biomarker level(s) or the calculation result based on which falls within or outside of X In some embodiments, when a single biomarker is used, the threshold score is a threshold level of the biomarker. More detailed description of the threshold level of a single biomarker is described in Section 4.2.1 below.

In other embodiments, when two or more biomarkers are used, the threshold score is a threshold composite score based on the levels of the two or more biomarkers. More detailed description of the threshold composite score based on the levels of two or more biomarkers is described in Section 4.2.2 below.

4.2.1 Using a Single Biomarker for Identifying a Subject Who is Likely to be Responsive to a PDE4 Inhibitor, or Predicting the Responsiveness of a Subject to a Treatment with a PDE4 Inhibitor As described in Section 5.1 and 5.2 below, a single biomarker, e.g., MCP1, can sufficiently differentiate a group of patients with higher response rate to PDE4 inhibitor treatment. Thus, in one aspect, provided herein are methods for using a single biomarker identified in the present disclosure, e.g., those listed in Table 3, for predicting a patient's responsiveness to a treatment with a PDE4 inhibitor, e.g., apremilast.

In certain embodiments, provided herein is a method of identifying a subject having a disease or disorder who is likely to be responsive to a treatment with apremilast, or predicting the responsiveness of a subject having or suspected of having a disease or disorder to a treatment with apremilast, comprising:

(a) obtaining a sample from the subject;
(b) measuring the level of a biomarker in the sample; and
(c) diagnosing the subject as being likely to be responsive to apremilast if the level of the biomarker in the sample is lower or higher as compared with a threshold level of the biomarker, or correlating the level of the biomarker in the sample with a likelihood of the subject being responsive to treatment with apremilast.

In some embodiments, the biomarker is selected from the group consisting of Alpha-1-Antitrypsin, Alpha-2-Macroglobulin, Beta-2-Microglobulin, Brain-Derived Neurotrophic Factor, C-Reactive Protein, Complement C3, Eotaxin-1, Factor VII, Ferritin, Fibrinogen, Granulocyte-Macrophage Colony-Stimulating Factor, Haptoglobin, Intercellular Adhesion Molecule 1, Interferon gamma, Interleukin-1 alpha, Interleukin-1 beta, Interleukin-1 receptor antagonist, Interleukin-10, Interleukin-12 Subunit p40, Interleukin-12 Subunit p'70, Interleukin-15, Interleukin-17, Interleukin-2, Interleukin-23, Interleukin-3, Interleukin-4, Interleukin-5, Interleukin-6, Interleukin-7, Interleukin-8, Macrophage Inflammatory Protein-1 alpha, Macrophage Inflammatory Protein-1 beta, Matrix Metalloproteinase-3, Matrix Metalloproteinase-9, MCP1, Stem Cell Factor, T-Cell-Specific Protein RANTES, Tissue Inhibitor of Metalloproteinases, Tumor Necrosis Factor alpha, Tumor Necrosis Factor beta, Tumor necrosis factor receptor 2, Vascular Cell Adhesion Molecule-1, Vascular Endothelial Growth Factor, Vitamin D-Binding Protein, von Willebrand Factor, Osteoprotegerin, Interleukin-18, Receptor Activator of Nuclear Factor Kappa B Ligand (RANKL), and Sclerostin.

In other embodiments, the biomarker is selected from the group consisting of MCP1, Interleukin-15, C-Reactive Protein, Matrix Metalloproteinase-3, Interleukin-1 receptor antagonist, von Willebrand Factor, Eotaxin-1, Alpha-1-Antitrypsin, Macrophage Inflammatory Protein-1 beta, Vascular Cell Adhesion Molecule-1, Tissue Inhibitor of Metalloproteinases 1, Osteoprotegerin, Vascular Endothelial Growth Factor, Alpha-2-Macroglobulin, Brain-Derived Neurotrophic Factor, Intercellular Adhesion Molecule 1, Interleukin-18, Matrix Metalloproteinase-9, and Vitamin D-Binding Protein.

In one embodiment, the biomarker is MCP1. In one embodiment, the biomarker is Interleukin-15. In one embodiment, the biomarker is C-Reactive Protein. In one embodiment, the biomarker is Matrix Metalloproteinase-3. In one embodiment, the biomarker is Interleukin-1 receptor antagonist. In one embodiment, the biomarker is von Willebrand Factor. In one embodiment, the biomarker is Eotaxin-1. In one embodiment, the biomarker is Alpha-1-Antitrypsin. In one embodiment, the biomarker is Macrophage Inflammatory Protein-1 beta. In one embodiment, the biomarker is Vascular Cell Adhesion Molecule-1. In one embodiment, the biomarker is Tissue Inhibitor of Metalloproteinases 1. In one embodiment, the biomarker is Osteoprotegerin. In one embodiment, the biomarker is Vascular Endothelial Growth Factor. In one embodiment, the biomarker is Alpha-2-Macroglobulin. In one embodiment, the biomarker is Brain-Derived Neurotrophic Factor. In one embodiment, the biomarker is Intercellular Adhesion Molecule 1. In one embodiment, the biomarker is Interleukin-18. In one embodiment, the biomarker is Matrix Metalloproteinase-9. In one embodiment, the biomarker is Vitamin D-Binding Protein.

As shown in Section 5.2 below, MCP1 is identified as the biomarker that associates with the group of ankylosing spondylitis patients which have a higher response rate to Apremilast than the remaining ankylosing spondylitis patients treated with apremilast. Thus, in some specific embodiments, provided herein is a method of identifying a subject having ankylosing spondylitis who is likely to be responsive to a treatment with apremilast, or predicting the responsiveness of a subject having or suspected of having ankylosing spondylitis to a treatment with apremilast, comprising:

(a) obtaining a sample from the subject;
(b) measuring the level of MCP1 in the sample; and
(c) diagnosing the subject as being likely to be responsive to apremilast if the level of MCP1 in the sample is lower than a threshold level of MCP1, or correlating the level of MCP1 in the sample with a likelihood of the subject being responsive to treatment with apremilast As shown in the Section 5.1 and Table 1, certain biomarkers are expressed at a lower level in the group of patients likely to be responsive to the apremilast treatment, such as MCP1, Interleukin-8, Macrophage Inflammatory Protein-1 beta, Eotaxin-1, Vascular Cell Adhesion Molecule-1, Interleukin-18, Sclerostin, Tissue Inhibitor of Metalloproteinases, and Osteoprotegerin. Other biomarkers are expressed at a higher levels in the group of patients likely to be responsive to the apremilast treatment, such as von Willebrand Factor, C-Reactive Protein, Alpha-1-Antitrypsin, Interleukin-1 receptor antagonist, Interleukin-15, Fibrinogen, Matrix Metalloproteinase-3, Complement C3, and Haptoglobin.

Thus, in some embodiments, the subject is determined as being likely to be responsive to apremilast if the level of the biomarker in the sample is lower than a threshold level of the biomarker, and the biomarker is MCP1, Interleukin-8, Macrophage Inflammatory Protein-1 beta, Eotaxin-1, Vascular Cell Adhesion Molecule-1, Interleukin-18, Sclerostin, Tissue Inhibitor of Metalloproteinases, or Osteoprotegerin. In a specific embodiment, the biomarker is MCP1, and the subject is diagnosed as being likely to be responsive to apremilast if the level of MCP1 in the sample is lower than a threshold level of MCP1.

In some specific embodiments, the methods comprise determining the subject as being likely to be responsive to treatment with apremilast if the level of MCP1 of the patient is lower than a threshold level of MCP1, and the threshold level of the MCP1 is between about 150 pg/ml to about 70 pg/ml. In another embodiment, the threshold level of MCP1 is between about 110 pg/ml to about 75 pg/ml. In other embodiments, the threshold level of MCP1 is between about 95 pg/ml to about 75 pg/ml. In some embodiments, the threshold level of MCP1 is about 105 pg/ml, 95 pg/ml, or 75 pg/ml. In other embodiments, the threshold level of MCP1 is lower than 70 pg/ml, such as 65 pg/ml, 60 pg/ml, 55 pg/ml, 50 pg/ml, 45 pg/ml, 40 pg/ml, 30 pg/ml, 25 pg/ml, 20 pg/ml, and 10 pg/ml. In a specific embodiment, the threshold level of MCP1 is about 105 pg/ml. In another specific embodiment, the threshold level of MCP1 is about 95 pg/ml. In another specific embodiment, the threshold level of MCP1 is about 75 pg/ml.

In other embodiments, the subject is determined as being likely to be responsive to apremilast if the level of the biomarker in the sample is higher than a threshold level of the biomarker, and the biomarker is Willebrand Factor, C-Reactive Protein, Alpha-1-Antitrypsin, Interleukin-1 receptor antagonist, Interleukin-15, Fibrinogen, Matrix Metalloproteinase-3, Complement C3, or Haptoglobin.

It should be noted that the value of the threshold level of a single biomarker may affect the likelihood of a patient's responsiveness to the treatment with apremilast. In some embodiments, a lower threshold level of a single biomarker is correlated with a higher response rate. In other embodiments, a higher threshold level of a single biomarker is correlated with a higher response.

In certain embodiments as illustrated in Section 5.2.1 below, the threshold level of a single biomarker can be determined based on the levels of the biomarker in a population of subjects. In some embodiments, the threshold level of the biomarker is calculated as the average or median of the biomarker levels in the population. In other embodiments, the threshold level of the biomarker is determined based on the levels of the biomarker of the subjects that are responsive or are likely to be responsive to apremilast and the levels of the biomarker of those subjects that are not responsive or are not likely to be responsive to apremilast. In a more specific embodiment, the threshold level of the biomarker is determined as the mid-point between the median level of the biomarker of the patients that are likely to be responsive to apremilast and the median level of the biomarker of the patients that are not likely to be responsive to apremilast. In yet other embodiments, the threshold level of the biomarker is calculated as mean of thresholds obtained from cross validation (e.g., 3-fold, 5-fold, or 10-fold cross validation). In other embodiments, the threshold level of the biomarker is calculated as mean of thresholds obtained from 3-fold, 4-fold, 5-fold, 6-fold, 10-fold, 20-fold, or 50-fold cross validation. In one embodiment, the threshold level of the biomarker is calculated as mean of thresholds obtained from 3-fold cross validation. In other embodiments, the threshold level of the biomarker is calculated as mean of thresholds obtained from 4-fold cross validation. In yet other embodiments, the threshold level of the biomarker is calculated as mean of thresholds obtained from 5-fold cross validation. In yet other embodiments, the threshold level of the biomarker is calculated as mean of thresholds obtained from 6-fold cross validation. In yet other embodiments, the threshold level of the biomarker is calculated as mean of thresholds obtained from 10-fold cross validation. In yet other embodiments, the threshold level of the biomarker is calculated as mean of thresholds obtained from 20-fold cross validation. In yet other embodiments, the threshold level of the biomarker is calculated as mean of thresholds obtained from 50-fold cross validation. The fold number can be more than 50, and can be various depending on the size of the population.

In certain embodiments, the subject is diagnosed as having more than 50% to 90% likelihood to be responsive to a treatment with apremilast, if the level of the biomarker is lower or higher as compared with the threshold level of the biomarker. In one embodiment, the subject is diagnosed as having more than 50% likelihood to be responsive to a treatment with apremilast, if the level of the biomarker is lower or higher as compared with the threshold level of the biomarker. In another embodiment, the subject is diagnosed as having more than 60% likelihood to be responsive to a treatment with apremilast, if the level of the biomarker is lower or higher as compared with the threshold level of the biomarker. In another embodiment, the subject is diagnosed as having more than 70% likelihood to be responsive to a treatment with apremilast, if the level of the biomarker is lower or higher as compared with the threshold level of the biomarker. In yet another embodiment, the subject is diagnosed as having more than 80% likelihood to be responsive to a treatment with apremilast, if the level of the biomarker is lower or higher as compared with the threshold level of the biomarker. In yet another embodiment, the subject is diagnosed as having more than 90% likelihood to be responsive to a treatment with apremilast, if the level of the biomarker is lower or higher as compared with the threshold level of the biomarker.

In some more specific embodiments, the biomarker is MCP1, and the subject is diagnosed as having more than 50% likelihood to be responsive to apremilast if the level of MCP1 is lower than the threshold level of MCP1. In some more specific embodiments, the biomarker is MCP1, and the subject is diagnosed as having more than 55% likelihood to be responsive to apremilast if the level of MCP 1 is lower than the threshold level of MCP 1. In some more specific embodiments, the biomarker is MCP1, and the subject is diagnosed as having more than 60% likelihood to be responsive to apremilast if the level of MCP1 is lower than the threshold level of MCP1. In some more specific embodiments, the biomarker is MCP1, and the subject is diagnosed as having more than 65% likelihood to be responsive to apremilast if the level of MCP1 is lower than the threshold level of MCP1. In some more specific embodiments, the biomarker is MCP1, and the subject is diagnosed as having more than 70% likelihood to be responsive to apremilast if the level of MCP1 is lower than the threshold level of MCP1. In some more specific embodiments, the biomarker is MCP1, and the subject is diagnosed as having more than 80% likelihood to be responsive to apremilast if the level of MCP1 is lower than the threshold level of MCP1. In some more specific embodiments, the biomarker is MCP1, and the subject is diagnosed as having more than 90% likelihood to be responsive to apremilast if the level of MCP 1 is lower than the threshold level of MCP 1.

4.2.2 Using Multiple Biomarkers for Identifying a Subject Who is Likely to be Responsive to a PDE4 Inhibitor, or Predicting the Responsiveness of a Subject to a Treatment with a PDE4 Inhibitor As described in Sections 5.1 and 5.3 below, an expression profile of 49 biomarkers or a subset thereof (multiple biomarkers) can be used to differentiate a group of patients having higher response rate to apremilast. For example, the combination of the top 2 biomarkers identified in the present study, the combination of the top 5 biomarkers, the combination of the top 10 biomarkers, or the combination of all the 49 biomarkers can be used to group a patient for the purpose of predicting a patient's response, as demonstrated in Section 5.3 and FIGS. 3B-3E.

Thus, also provided herein are methods of using multiple biomarkers (two or more biomarkers) for identifying a subject who is likely to be responsive to apremilast, or predicting the responsiveness of a subject to a treatment with apremilast. In certain embodiments, provided herein is a method of identifying a subject having a disease or disorder who is likely to be responsive to a treatment with apremilast, or predicting the responsiveness of a subject having or suspected of having a disease or disorder to a treatment with apremilast, comprising:

(a) obtaining a sample from the subject;
(b) measuring the levels of two or more biomarkers in the sample; and
(c) correlating the levels of two or more biomarkers with a likelihood of the subject being responsive to treatment with apremilast.

In some embodiments, 2 to 49 biomarkers are used to predict a patient's response. Any range therein is also contemplated. In one embodiment, 2 biomarkers are used to predict a patient's response. In one embodiment, 3 biomarkers are used to predict a patient's response. In one embodiment, 4 biomarkers are used to predict a patient's response. In one embodiment, 5 biomarkers are used to predict a patient's response. In another embodiment, 6 biomarkers are used to predict a patient's response. In another embodiment, 7 biomarkers are used to predict a patient's response. In yet another embodiment, 8 biomarkers are used to predict a patient's response. In yet another embodiment, 9 biomarkers are used to predict a patient's response. In yet another embodiment, 10 biomarkers are used to predict a patient's response. In yet another embodiment, 49 biomarkers are used to predict a patient's response.

In some embodiments, the two or more biomarkers are independently selected from the group consisting of Alpha-1-Antitrypsin, Alpha-2-Macroglobulin, Beta-2-Microglobulin, Brain-Derived Neurotrophic Factor, C-Reactive Protein, Complement C3, Eotaxin-1, Factor VII, Ferritin, Fibrinogen, Granulocyte-Macrophage Colony-Stimulating Factor, Haptoglobin, Intercellular Adhesion Molecule 1, Interferon gamma, Interleukin-1 alpha, Interleukin-1 beta, Interleukin-1 receptor antagonist, Interleukin-10, Interleukin-12 Subunit p40, Interleukin-12 Subunit p70, Interleukin-15, Interleukin-17, Interleukin-2, Interleukin-23, Interleukin-3, Interleukin-4, Interleukin-5, Interleukin-6, Interleukin-7, Interleukin-8, Macrophage Inflammatory Protein-1 alpha, Macrophage Inflammatory Protein-1 beta, Matrix Metalloproteinase-3, Matrix Metalloproteinase-9, MCP1, Stem Cell Factor, T-Cell-Specific Protein RANTES, Tissue Inhibitor of Metalloproteinases, Tumor Necrosis Factor alpha, Tumor Necrosis Factor beta, Tumor necrosis factor receptor 2, Vascular Cell Adhesion Molecule-1, Vascular Endothelial Growth Factor, Vitamin D-Binding Protein, von Willebrand Factor, Osteoprotegerin, Interleukin-18, RANKL, and Sclerostin.

In one embodiment, the two or more biomarkers are independently selected from the group consisting of MCP1, Interleukin-15, C-Reactive Protein, Matrix Metalloproteinase-3, Interleukin-1 receptor antagonist, von Willebrand Factor, Eotaxin-1, Alpha-1-Antitrypsin, Macrophage Inflammatory Protein-1 beta, Vascular Cell Adhesion Molecule-1, Tissue Inhibitor of Metalloproteinases 1, Osteoprotegerin, Vascular Endothelial Growth Factor, Alpha-2-Macroglobulin, Brain-Derived Neurotrophic Factor, Intercellular Adhesion Molecule 1, Interleukin-18, Matrix Metalloproteinase-9, and Vitamin D-Binding Protein.

In a specific embodiment, one of the two or more biomarkers is MCP1, thus in another embodiment, provided herein is a method of identifying a subject having a disease or disorder who is likely to be responsive to apremilast, or predicting the responsiveness of a subject having or suspected of having a disease or disorder to apremilast, comprising:

(a) obtaining a sample from the subject;
(b) determining the levels of two or more biomarkers in the sample, wherein one of the two or more biomarkers is MCP1;
(c) correlating the levels of the two or more biomarkers with a likelihood of the subject being responsive to treatment with apremilast.

In some embodiments, the two or more biomarkers are MCP1 and Interleukin-15. In some embodiments, the two or more biomarkers are MCP1, Interleukin-15, and C-Reactive Protein. In other embodiments, the two or more biomarkers are MCP1, Interleukin-15, C-Reactive Protein, and Matrix Metalloproteinase-3. In other embodiments, the two or more biomarkers are MCP1, Interleukin-15, C-Reactive Protein, Matrix Metalloproteinase-3, and Interleukin-1 receptor antagonist. In yet other embodiments, the two or more biomarkers are MCP1, Interleukin-15, C-Reactive Protein, Matrix Metalloproteinase-3, Interleukin-1 receptor antagonist, and von Willebrand Factor. In yet other embodiments, the two or more biomarkers are MCP1, Interleukin-15, C-Reactive Protein, Matrix Metalloproteinase-3, Interleukin-1 receptor antagonist, von Willebrand Factor, and Eotaxin-1. In yet other embodiments, the two or more biomarkers are MCP1, Interleukin-15, C-Reactive Protein, Matrix Metalloproteinase-3, Interleukin-1 receptor antagonist, von Willebrand Factor, Eotaxin-1, and Alpha-1-Antitrypsin. In yet other embodiments, the two or more biomarkers are MCP1, Interleukin-15, C-Reactive Protein, Matrix Metalloproteinase-3, Interleukin-1 receptor antagonist, von Willebrand Factor, Eotaxin-1, Alpha-1-Antitrypsin, and Macrophage Inflammatory Protein-1 beta. In yet other embodiments, the two or more biomarkers are MCP1, Interleukin-15, C-Reactive Protein, Matrix Metalloproteinase-3, Interleukin-1 receptor antagonist, von Willebrand Factor, Eotaxin-1, Alpha-1-Antitrypsin, Macrophage Inflammatory Protein-1 beta, and Vascular Cell Adhesion Molecule-1.

In certain embodiments, the step of correlating the levels of the two or more biomarkers with a likelihood of the subject being responsive to treatment with apremilast comprises (a) generating a threshold composite score based upon the levels of two or more biomarker levels measured in a population having the disease or disorder; and (b) determining the likelihood of a subject being responsive to apremilast by comparing the threshold composite score to the composite score of the subject.

In more specific embodiments, the step of correlating the levels of the two or more biomarkers with a likelihood of the subject being responsive to treatment with apremilast comprises (a) determining the expression profile of the biomarkers provided herein or a subset thereof in a biological sample from a population of subjects that previously have been administered with apremilast, wherein each subset of the biomarkers corresponds to biomarkers differentially expressed by the subjects; (b) generating a composite score for the biomarkers or the subset thereof for each subject of the population; (c) differentiating the subjects that are responsive to or are likely to be responsive to apremilast from those subjects that are not responsive to or are not likely to be responsive to apremilast; and (d) determining responsiveness to apremilast based on the composite scores for the subjects that are responsive to or are likely to be responsive to apremilast and those subjects that are not responsive to or are not likely to be responsive to apremilast.

In another more specific embodiments, the step of correlating the levels of the two or more biomarkers with a likelihood of the subject being responsive to treatment with apremilast comprises (a) determining the expression profile of the biomarkers provided herein or a subset thereof in a biological sample from a population of subjects that previously have been administered with apremilast, wherein each subset of the biomarkers corresponds to biomarkers differentially expressed by the subjects; (b) generating a composite score for the biomarkers or the subset thereof for each subject of the population; (c) differentiating the subjects that are responsive to or are likely to be responsive to apremilast from those subjects that are not responsive to or are not likely to be responsive to apremilast; (d) generating a threshold composite score that is predictive of the responsiveness of a subject to apremilast using a model based on the composite scores for the subjects that are responsive to or are likely to be responsive to apremilast and those subjects that are not responsive to are not likely to be responsive to apremilast, and (e) determining the likelihood of a subject being responsive to apremilast by comparing the threshold composite score to the composite score of the subject.

In some embodiments, a classifier can be used to correlate the levels of the two or more biomarkers with a likelihood of the subject being responsive to treatment with apremilast. Any classifier that classifies based on two or more features (i.e., assigning a sample into a group based on two or more features of the sample) can be used in the present disclosure. In some embodiments, the classifier is a supervised classification algorithm. Unlimited examples of such classifiers include standard SVM, random forest, decision trees, rule based classifiers and discriminate analysis. Other classifiers, known to those skilled in the art, that can analyze the expression profile of multiple biomarkers from a population in order to "learn" a decision boundary between the patients likely to be responsive to a treatment compound and those patients not likely to be responsive to the treatment compound, are also included in the present disclosure.

In a specific embodiment, the classifier is Naive Bayes, and Naive Bayes is used to classify a patient based on two or more biomarker levels. In another specific embodiment, the classifier is Weighted RSVM, and Weighted RSVM is used to classify a patient based on two or more biomarker levels.

As explained in Section 5.3, Naive Bayes learns a probabilistic model between features and cluster membership that maximizes the posterior probability of the observed subgroups given the features (assuming independence of all features). The formula for Naive Bayes is:

$$\hat{y} = \underset{k \in \{1,\ldots,K\}}{\operatorname{argmax}} \, p(C_k) \prod_{i=1}^{n} p(x_i \mid C_k),$$

where $p(C_k)$ represents overall class (MCP1 low cluster membership) probability, K is number of classes (here two), n is the number of features (number of biomarkers used (2 for Top 2, etc)), x are the features themselves and $p(x_i|C_k)$ is the posterior probability of observing $x_i$ given class $C_k$.

SVM (support vector machine) is a classifier that draws a boundary between MCP1 low and non-MCP1low clusters. Weighted RSVM is weighted reduced SVM. Reduced version of SVM uses a subset of the data to improve efficiency and generalization of the model. Weighted version balances classes of different sizes. The formula of SVM is $$f(\vec{x}) = \operatorname{sign}(\Sigma a_i y_i K(\vec{x}_i, \vec{x}) + b)$$

where $x_i$ is a sample represented by a vector of features and x is all the samples, K is a kernel matrix which encodes the distance between all samples, $y_i$ is the cluster membership for sample i, alpha is an indicator variable that describes which samples are closest to the classification boundary and b is an offset.

In some embodiments, the levels of the two or more biomarkers are correlated with a greater than 50%, 60%, 70%, 80% or 90% likelihood of the subject being responsive to apremilast. In some embodiments, the levels of the two or more biomarkers are correlated with a greater than 50% likelihood of the subject being responsive to apremilast. In one embodiment, the levels of the two or more biomarkers are correlated with a greater than 60% likelihood of the subject being responsive to apremilast. In another embodiment, the levels of the two or more biomarkers are correlated with a greater than 70% likelihood of the subject being responsive to apremilast. In some embodiments, the levels of the two or more biomarkers are correlated with a greater than 80% likelihood of the subject being responsive to apremilast. In one embodiment, the levels of the two or more biomarkers are correlated with a greater than 90% likelihood of the subject being responsive to apremilast.

4.2.3 Methods of Treatment, Management or Prevention

In another aspect, provided herein are methods of treating, managing and/or preventing an inflammatory disease or related disorders, which comprise administering to a patient in need of such treatment, management or prevention a therapeutically or prophylactically effective amount of a PDE4 inhibitor, e.g., apremilast. In one embodiment, the method is a method of treating an inflammatory disease or a related disorder. In one embodiment, the method is a method of managing an inflammatory disease or a related disorder. In one embodiment, the method is a method of preventing an inflammatory disease or a related disorder. In one embodiment, the inflammatory disease is ankylosing spondylitis.

In some embodiments, provided herein are methods for treating a subject determined to be likely to be responsive to apremilast with apremilast. In one embodiment of the various methods provided herein, the methods comprise administering apremilast to the subject determined to be likely to be responsive to apremilast using the methods provided herein, e.g., those described in Sections 4.2.1 and 4.2.2. Thus, in some embodiments, provided herein is a method of treating a subject, comprising:

(a) identifying the subject as having a disease or disorder that may be responsive to a treatment with apremilast, comprising:
 (i) obtaining a sample from the subject;
 (ii) measuring the level(s) of one or more biomarker(s) in the sample; and
 (iii) correlating the level(s) of the one or more biomarker(s) with a likelihood of the subject being responsive to treatment with apremilast; and
(b) administering the subject a therapeutically effective amount of apremilast if the subject is identified as being likely to be responsive to treatment with apremilast.

In some embodiments, the one or more biomarkers is independent selected from the group consisting of Alpha-1-Antitrypsin, Alpha-2-Macroglobulin, Beta-2-Microglobulin, Brain-Derived Neurotrophic Factor, C-Reactive Protein, Complement C3, Eotaxin-1, Factor VII, Ferritin, Fibrinogen, Granulocyte-Macrophage Colony-Stimulating Factor, Haptoglobin, Intercellular Adhesion Molecule 1, Interferon gamma, Interleukin-1 alpha, Interleukin-1 beta, Interleukin-1 receptor antagonist, Interleukin-10, Interleukin-12 Subunit p40, Interleukin-12 Subunit p'70, Interleukin-15, Interleukin-17, Interleukin-2, Interleukin-23, Interleukin-3, Interleukin-4, Interleukin-5, Interleukin-6, Interleukin-7, Interleukin-8, Macrophage Inflammatory Protein-1 alpha, Macrophage Inflammatory Protein-1 beta, Matrix Metalloproteinase-3, Matrix Metalloproteinase-9, MCP1, Stem Cell Factor, T-Cell-Specific Protein RANTES, Tissue Inhibitor of Metalloproteinases, Tumor Necrosis Factor alpha, Tumor Necrosis Factor beta, Tumor necrosis factor receptor 2, Vascular Cell Adhesion Molecule-1, Vascular Endothelial Growth Factor, Vitamin D-Binding Protein, von Willebrand Factor, Osteoprotegerin, Interleukin-18, RANKL, and Sclerostin.

In certain embodiments, the disease or disorder is selected from the group consisting of psoriasis, psoriatic arthritis, rheumatoid arthritis, rheumatoid spondylitis, osteoarthritis, other arthritic conditions, non-radiographic axial spondyloarthropathy, Crohn's disease, inflammatory bowel disease, ulcerative colitis, celiac disease, atopic dermatitis, and multiple sclerosis. In some embodiments, the disease or disorder is a chronic inflammatory disease. In some embodiments, the inflammatory disease is ankylosing spondylitis.

In some embodiments, the patient is an adult. In one embodiment, the patient is a newborn. In some embodiments, the patient is an infant. In another embodiment, the patient is a child. In one embodiment, the patient is an adolescent.

In certain embodiments, about 5 mg to about 100 mg of apremilast is administered to the subject per day. In one embodiment, about 10 mg to about 60 mg of apremilast is administered to the subject per day. In some embodiments, apremilast is administered to the subject once or twice daily. In some embodiments, about 5 mg to about 50 mg of apremilast is administered to the subject for 6 or more days. In one embodiment, about 10 mg to about 100 mg of apremilast is administered to the subject 6 or more days. It should be understood that the specific amount and administration frequency and duration will depend on the age of the subject being treated, the severity and stage of disease and the amount(s) of any optional additional second active agents concurrently administered to the patient.

4.4 Methods of Measuring Biomarker Levels

Biomarker levels (e.g., levels of cytokines) can be determined by measuring mRNA or protein levels of the biomarkers.

Several methods of detecting or quantitating mRNA levels are known in the art. Exemplary methods include, but are not limited to, northern blots, ribonuclease protection assays, PCR-based methods, and the like. The mRNA sequence of a biomarker can be used to prepare a probe that is at least partially complementary to the mRNA sequence. The probe can then be used to detect the mRNA in a sample, using any suitable assay, such as PCR-based methods, northern blotting, a dipstick assay, and the like.

In other embodiments, a nucleic acid assay can be prepared. An assay typically contains a solid support and at least one nucleic acid contacting the support, where the nucleic acid corresponds to at least a portion of an mRNA of a biomarker. The assay can also have a means for detecting the altered expression of the mRNA in the sample.

The assay method can be varied depending on the type of mRNA information desired. Exemplary methods include but are not limited to Northern blots and PCR-based methods (e.g., qRT-PCR). Methods, such as qRT-PCR, can also accurately quantitate the amount of the mRNA in a sample.

Any suitable assay platform can be used to determine the presence and amount of mRNA in a sample. For example, an assay may be in the form of a dipstick, a membrane, a chip, a disk, a test strip, a filter, a microsphere, a slide, a multi-well plate, or an optical fiber. An assay system may have a solid support on which a nucleic acid corresponding to the mRNA is attached. The solid support may comprise, for example, a plastic, silicon, a metal, a resin, glass, a membrane, a particle, a precipitate, a gel, a polymer, a sheet, a sphere, a polysaccharide, a capillary, a film, a plate, or a slide. The assay components can be prepared and packaged together as a kit for detecting or measuring an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.). See, e.g., Ausubel et al., *Short Protocols in Molecular Biology* (Wiley & Sons, 3rd ed. 1995); Sambrook et al., *Molecular Cloning: A Laboratory Manual* (Cold Spring Harbor, N.Y., 3rd ed. 2001). In another embodiment, the sample is labeled with fluorescent label. Exemplary fluorescent dyes include, but are not limited to, xanthene dyes, fluorescein dyes (e.g., fluorescein isothiocyanate (FITC), 6-carboxyfluorescein (FAM), 6 carboxy-2', 4',7',4,7-hexachlorofluorescein (HEX), 6-carboxy-4',5'-dichloro-2',7'-dimethoxyfluorescein (JOE)), rhodamine dyes (e.g., rhodamine 110 (R110), N,N,N',N'-tetramethyl-6-carboxyrhodamine (TAMRA), 6-carboxy-X-rhodamine (ROX), 5-carboxyrhodamine 6G (R6G5 or G5), 6-carboxyrhodamine 6G (R6G6 or G6)), cyanine dyes (e.g., Cy3, Cy5 and Cy7), Alexa dyes (e.g., Alexa-fluor-555), coumarin, Diethylaminocoumarin, umbelliferone, benzimide dyes (e.g., Hoechst 33258) phenanthridine dyes (e.g., Texas Red), ethidium dyes, acridine dyes, carbazole dyes, phenoxazine dyes, porphyrin dyes, polymethine dyes, BODIPY dyes, quinoline dyes, Pyrene, Fluorescein Chlorotriazinyl, eosin dyes, Tetramethylrhodamine, Lissamine, Napthofluorescein, and the like.

In one embodiment, the mRNA sequences comprise at least one mRNA of a biomarker provided herein. In some embodiments, the biomarker is selected from the group consisting of the mRNA of Alpha-1-Antitrypsin, Alpha-2-Macroglobulin, Beta-2-Microglobulin, Brain-Derived Neurotrophic Factor, C-Reactive Protein, Complement C3, Eotaxin-1, Factor VII, Ferritin, Fibrinogen, Granulocyte-Macrophage Colony-Stimulating Factor, Haptoglobin, Intercellular Adhesion Molecule 1, Interferon gamma, Interleukin-1 alpha, Interleukin-1 beta, Interleukin-1 receptor antagonist, Interleukin-10, Interleukin-12 Subunit p40, Interleukin-12 Subunit p70, Interleukin-15, Interleukin-17, Interleukin-2, Interleukin-23, Interleukin-3, Interleukin-4, Interleukin-5, Interleukin-6, Interleukin-7, Interleukin-8, Macrophage Inflammatory Protein-1 alpha, Macrophage Inflammatory Protein-1 beta, Matrix Metalloproteinase-3, Matrix Metalloproteinase-9, MCP1, Stem Cell Factor, T-Cell-Specific Protein RANTES, Tissue Inhibitor of Metalloproteinases, Tumor Necrosis Factor alpha, Tumor Necrosis Factor beta, Tumor necrosis factor receptor 2, Vascular Cell Adhesion Molecule-1, Vascular Endothelial Growth Factor, Vitamin D-Binding Protein, von Willebrand Factor, Osteoprotegerin, Interleukin-18, RANKL, and Sclerostin.

In a specific embodiment, the biomarker is the mRNA of MCP1. In a specific embodiment, the biomarker is the mRNA of Interleukin-15. In a specific embodiment, the biomarker is the mRNA of C-Reactive Protein. In a specific embodiment, the biomarker is the mRNA of Matrix Metalloproteinase-3. In a specific embodiment, the biomarker is the mRNA of Interleukin-1 receptor antagonist. In a specific embodiment, the biomarker is the mRNA of von Willebrand Factor. In a specific embodiment, the biomarker is the mRNA of Eotaxin-1. In a specific embodiment, the biomarker is the mRNA of Alpha-1-Antitrypsin. In a specific embodiment, the biomarker is the mRNA of Macrophage Inflammatory Protein-1 beta. In a specific embodiment, the biomarker is the mRNA of Vascular Cell Adhesion Molecule-1. In a specific embodiment, the biomarker is the mRNA of Tissue Inhibitor of Metalloproteinases 1. In a specific embodiment, the biomarker is the mRNA of Osteoprotegerin. In a specific embodiment, the biomarker is the mRNA of Vascular Endothelial Growth Factor. In a specific embodiment, the biomarker is the mRNA of Alpha-2-Macroglobulin. In a specific embodiment, the biomarker is the mRNA of Brain-Derived Neurotrophic Factor. In a specific embodiment, the biomarker is the mRNA of Intercellular Adhesion Molecule 1. In a specific embodiment, the biomarker is the mRNA of Interleukin-18. In a specific embodiment, the biomarker is the mRNA of Matrix Metalloproteinase-9. In a specific embodiment, the biomarker is the mRNA of Vitamin D-Binding Protein.

The nucleic acids may be present in specific, addressable locations on a solid support, each corresponding to at least a portion of mRNA sequence of a biomarker in a cell or a patient.

A typical mRNA assay method can contain the steps of 1) obtaining surface-bound subject probes; 2) hybridizing a population of mRNAs to the surface-bound probes under conditions sufficient to provide for specific binding; (3) post-hybridization washing to remove nucleic acids not specifically bound to the surface-bound probes; and (4) detecting the hybridized mRNAs. The reagents used in each of these steps and their conditions for use may vary depending on the particular application.

Hybridization can be carried out under suitable hybridization conditions, which may vary in stringency as desired. Typical conditions are sufficient to produce probe/target complexes on a solid surface between complementary binding members, i.e., between surface-bound subject probes and complementary mRNAs in a sample. In certain embodiments, stringent hybridization conditions may be employed.

Hybridization is typically performed under stringent hybridization conditions. Standard hybridization techniques (e.g., under conditions sufficient to provide for specific binding of target mRNAs in the sample to the probes) are described in Kallioniemi et al., *Science* 258:818-821 (1992) and International Patent Application Publication No. WO 93/18186. Several guides to general techniques are available, e.g., Tijssen, *Hybridization with Nucleic Acid Probes*, Parts I and II (Elsevier, Amsterdam 1993). For descriptions of techniques suitable for in situ hybridizations, see Gall et al., *Meth. Enzymol.* 21:470-480 (1981); Angerer et al., *Genetic Engineering: Principles and Methods*, Vol 7, pgs 43-65 (Plenum Press, New York, Setlow and Hollaender, eds. 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art.

Those of ordinary skill will readily recognize that alternative but comparable hybridization and wash conditions can be utilized to provide conditions of similar stringency.

After the mRNA hybridization procedure, the surface bound polynucleotides are typically washed to remove unbound nucleic acids. Washing may be performed using any convenient washing protocol, where the washing conditions are typically stringent, as described above. The hybridization of the target mRNAs to the probes is then detected using standard techniques.

Other methods, such as PCR-based methods, can also be used to detect or measure the expression of a biomarker provided herein. Examples of PCR methods can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

In some embodiments, quantitative Reverse Transcription-PCR (qRT-PCR) can be used for both the detection and quantification of RNA targets (Bustin et al., *Clin. Sci.* 109:365-379 (2005)). Quantitative results obtained by qRT-PCR are generally more informative than qualitative data. Thus, in one embodiment, qRT-PCR-based assays can be useful to measure mRNA levels during cell-based assays. The qRT-PCR method is also useful to monitor patient therapy. Examples of qRT-PCR-based methods can be found, for example, in U.S. Pat. No. 7,101,663, which is incorporated by reference herein in its entirety.

In contrast to regular reverse transcriptase-PCR and analysis by agarose gels, qRT-PCR gives quantitative results. An additional advantage of qRT-PCR is the relative ease and convenience of use. Instruments for qRT-PCR, such as the Applied Biosystems 7500, are available commercially, so are the reagents, such as TagMan® Sequence Detection Chemistry. For example, TagMan® Gene Expression Assays can be used, following the manufacturer's instructions.

These kits are pre-formulated gene expression assays for rapid, reliable detection and quantification of human, mouse, and rat mRNA transcripts. An exemplary qRT-PCR program, for example, is 50° C. for 2 minutes, 95° C. for 10 minutes, 40 cycles of 95° C. for 15 seconds, then 60° C. for 1 minute.

To determine the cycle number at which the fluorescence signal associated with a particular amplicon accumulation crosses the threshold (referred to as the $C_T$), the data can be analyzed, for example, using a 7500 Real-Time PCR System Sequence Detection software v1.3 using the comparative $C_T$ relative quantification calculation method. Using this method, the output is expressed as a fold-change of expression levels. In another embodiment, the threshold level can be selected to be automatically determined by the software. In some embodiments, the threshold level is set to be above the baseline but sufficiently low to be within the exponential growth region of an amplification curve.

Several protein detection and quantitation methods can be used to measure the level of a biomarker. Any suitable protein quantitation method can be used. In one embodiment, antibody-based methods are used. Exemplary methods that can be used include, but are not limited to, immunoblotting (Western blot), ELISA, immunohistochemistry, flow cytometry, cytometric bead array, mass spectroscopy, and the like. Several types of ELISA are commonly used, including direct ELISA, indirect ELISA, and sandwich ELISA.

In some embodiments, the biomarker is selected from the group consisting of the protein of Alpha-1-Antitrypsin, Alpha-2-Macroglobulin, Beta-2-Microglobulin, Brain-Derived Neurotrophic Factor, C-Reactive Protein, Complement C3, Eotaxin-1, Factor VII, Ferritin, Fibrinogen, Granulocyte-Macrophage Colony-Stimulating Factor, Haptoglobin, Intercellular Adhesion Molecule 1, Interferon gamma, Interleukin-1 alpha, Interleukin-1 beta, Interleukin-1 receptor antagonist, Interleukin-10, Interleukin-12 Subunit p40, Interleukin-12 Subunit p70, Interleukin-15, Interleukin-17, Interleukin-2, Interleukin-23, Interleukin-3, Interleukin-4, Interleukin-5, Interleukin-6, Interleukin-7, Interleukin-8, Macrophage Inflammatory Protein-1 alpha, Macrophage Inflammatory Protein-1 beta, Matrix Metalloproteinase-3, Matrix Metalloproteinase-9, MCP1, Stem Cell Factor, T-Cell-Specific Protein RANTES, Tissue Inhibitor of Metalloproteinases, Tumor Necrosis Factor alpha, Tumor Necrosis Factor beta, Tumor necrosis factor receptor 2, Vascular Cell Adhesion Molecule-1, Vascular Endothelial Growth Factor, Vitamin D-Binding Protein, von Willebrand Factor, Osteoprotegerin, Interleukin-18, RANKL, and Sclerostin.

In a specific embodiment, the biomarker is the protein of MCP1. In a specific embodiment, the biomarker is the protein of Interleukin-15. In a specific embodiment, the biomarker is the protein of C-Reactive Protein. In a specific embodiment, the biomarker is the protein of Matrix Metalloproteinase-3. In a specific embodiment, the biomarker is the protein of Interleukin-1 receptor antagonist. In a specific embodiment, the biomarker is the protein of von Willebrand Factor. In a specific embodiment, the biomarker is the protein of Eotaxin-1. In a specific embodiment, the biomarker is the protein of Alpha-1-Antitrypsin. In a specific embodiment, the biomarker is the protein of Macrophage Inflammatory Protein-1 beta. In a specific embodiment, the biomarker is the protein of Vascular Cell Adhesion Molecule-1. In a specific embodiment, the biomarker is the protein of Tissue Inhibitor of Metalloproteinases 1. In a specific embodiment, the biomarker is the protein of Osteoprotegerin. In a specific embodiment, the biomarker is the protein of Vascular Endothelial Growth Factor. In a specific embodiment, the biomarker is the protein of Alpha-2-Macroglobulin. In a specific embodiment, the biomarker is the protein of Brain-Derived Neurotrophic Factor. In a specific embodiment, the biomarker is the protein of Intercellular Adhesion Molecule 1. In a specific embodiment, the biomarker is the protein of Interleukin-18. In a specific embodiment, the biomarker is the protein of Matrix Metalloproteinase-9. In a specific embodiment, the biomarker is the protein of Vitamin D-Binding Protein.

4.5 Kits for Detecting or Measuring Biomarker Levels

In certain embodiments, provided herein is a kit for detecting or measuring the mRNA level of one or more biomarkers. In certain embodiments, the kit comprises one or more probes that bind specifically to the mRNAs of the one or more biomarkers. In certain embodiments, the kit further comprises a washing solution. In certain embodiments, the kit further comprises reagents for performing a hybridization assay, mRNA isolation or purification means, detection means, as well as positive and negative controls. In certain embodiments, the kit further comprises an instruction for using the kit. The kit can be tailored for in-home use, clinical use, or research use.

In certain embodiments, provided herein is a kit for detecting the protein level of one or more biomarkers. In certain embodiments, the kits comprises a dipstick coated with an antibody that recognizes the protein biomarker, washing solutions, reagents for performing the assay, protein isolation or purification means, detection means, as well as positive and negative controls. In certain embodiments, the kit further comprises an instruction for using the kit. The kit can be tailored for in-home use, clinical use, or research use.

Such a kit can employ, for example, a dipstick, a membrane, a chip, a disk, a test strip, a filter, a microsphere, a slide, a multi-well plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an organ, an organelle, a biological fluid, a blood sample, a urine sample, or a skin sample.

In another embodiment, the kit comprises a solid support, nucleic acids attached to the support, where the nucleic acids are complementary to at least 20, 50, 100, 200, 350, or more bases of mRNA, and a means for detecting the expression of the mRNA in a biological sample.

In a specific embodiment, the pharmaceutical or assay kit comprises, in a container, a compound or a pharmaceutical composition thereof, and further comprises, in one or more containers, components for isolating RNA. In another specific embodiment, the pharmaceutical or assay kit comprises, in a container, a compound or a pharmaceutical composition, and further comprises, in one or more containers, components for conducting RT-PCR, qRT-PCR, deep sequencing, or microarray In certain embodiments, the kits provided herein employ means for detecting or measuring the expression of a biomarker by quantitative real-time PCR (qRT-PCR), microarray, flow cytometry, or immunofluorescence. In other embodiments, the expression of the biomarker is measured by ELISA-based methodologies or other similar methods known in the art.

In another specific embodiment, the pharmaceutical or assay kit comprises, in a container, a compound or a pharmaceutical composition thereof, and further comprises, in one or more containers, components for isolating protein. In another specific embodiment, the pharmaceutical or assay kit comprises, in a container, a compound or a pharmaceutical composition, and further comprises, in one or more containers, components for conducting flow cytometry or ELISA.

In another aspect, provided herein are kits for measuring biomarkers that supply the materials necessary to measure the abundance of one or more gene products of the biomarkers or a subset of the biomarkers (e.g., one, two, three, four, five, or more biomarkers) provided herein. Such kits may comprise materials and reagents required for measuring RNA or protein. In another embodiment, such kits include microarrays, wherein the microarray is comprised of oligonucleotides and/or DNA and/or RNA fragments which hybridize to one or more gene products of the biomarkers or a subset of the biomarkers provided herein, or any combination thereof. In one embodiment, such kits may include primers for PCR of either the RNA product or the cDNA copy of the RNA product of the biomarkers or a subset of the biomarkers, or both. In some embodiments, such kits may include primers for PCR as well as probes for qPCR. In some embodiments, such kits may include multiple primers and multiple probes, wherein some of the probes have different fluorophores so as to permit simultaneously measuring multiple gene products of the biomarkers or a subset of the biomarkers provided herein. In one embodiment, such kits may further include materials and reagents for creating cDNA from RNA. In another embodiment, such kits may include antibodies specific for the protein products of the biomarkers or a subset of the biomarkers provided herein. Such kits may additionally comprise materials and reagents for isolating RNA and/or proteins from a biological sample. In addition, such kits may include materials and reagents for synthesizing cDNA from RNA isolated from a biological sample. In some embodiments, such kits may include a computer program product embedded on computer readable media for predicting whether a patient is clinically sensitive to apremilast. In one embodiment, the kits may include a computer program product embedded on a computer readable media along with instructions.

In some embodiments, such kits measure the expression of one or more nucleic acid products of the biomarkers or a subset of the biomarkers provided herein. In accordance with this embodiment, the kits may comprise materials and reagents that are necessary for measuring the expression of particular nucleic acid products of the biomarkers or a subset of the biomarkers provided herein. For example, a microarray or RT-PCR kit may be produced for a specific condition and contain only those reagents and materials necessary for measuring the levels of specific RNA transcript products of the biomarkers or a subset of the biomarkers provided herein, to predict whether an inflammatory disease in a patient is clinically sensitive to apremilast. Alternatively, in another embodiment, the kits can comprise materials and reagents necessary for measuring the expression of particular nucleic acid products of genes other than the biomarkers provided herein. For example, in certain embodiments, the kits comprise materials and reagents necessary for measuring the expression levels of 1, 2, 3, 4, 5, 6, 7, 8, 9, 10, 15, 20, 25, 30, 35, 40, 45, 48 or more of the genes of the biomarkers provided herein, in addition to reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 48, or more genes other than the biomarkers provided herein. In other embodiments, the kits contain reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 48, or more of the biomarkers provided herein, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not the biomarkers provided herein. In certain embodiments, the kits contain reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 48, or more of the genes of the biomarkers provided herein, and 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000 genes that are not the biomarkers provided herein.

For nucleic acid microarray kits, the kits generally comprise probes attached to a solid support surface. In one such embodiment, probes can be either oligonucleotides or longer probes including probes ranging from 150 nucleotides to 800 nucleotides in length. The probes may be labeled with a detectable label. In a specific embodiment, the probes are specific for one or more of the gene products of the biomarkers provided herein. The microarray kits may comprise instructions for performing the assay and methods for interpreting and analyzing the data resulting from performing the assay. In a specific embodiment, the kits comprise instructions for predicting whether an inflammatory disease in a patient is clinically sensitive to apremilast. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own suitable container.

In certain embodiments, a nucleic acid microarray kit comprises materials and reagents necessary for measuring the expression levels of 1, 2, 3, 4, 5, 6, 7, 8, 9, 10, 15, 20, 25, 30, 35, 40, 45, 48, or more of the genes of the biomarkers provided herein, or a combination thereof, in addition to reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more genes other than those of the biomarkers provided herein. In other embodiments, a nucleic acid microarray kit contains reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 48, or more of the genes of the biomarkers provided herein, or any combination thereof, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not of the biomarkers provided herein. In another embodiment, a nucleic acid microarray kit contains reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 48, or more of the genes of the biomarkers provided herein, or any combination thereof, and 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000, or 500-1000 genes that are not of the biomarkers provided herein.

For quantitative PCR, the kits generally comprise pre-selected primers specific for particular nucleic acid sequences. The quantitative PCR kits may also comprise enzymes suitable for amplifying nucleic acids (e.g., polymerases, such as Taq polymerase), deoxynucleotides, and buffers needed for amplification reaction. The quantitative PCR kits may also comprise probes specific for the nucleic acid sequences associated with or indicative of a condition. The probes may or may not be labeled with a fluorophore. The probes may or may not be labeled with a quencher molecule. In one embodiment, the quantitative PCR kits also comprise components suitable for reverse-transcribing RNA, including enzymes (e.g., reverse transcriptases, such as AMV, MMLV, and the like) and primers for reverse transcription along with deoxynucleotides and buffers needed for reverse transcription reaction. Each component of the quantitative PCR kit is generally in its own suitable container. Thus, these kits generally comprise distinct containers suitable for each individual reagent, enzyme, primer and probe. Further, the quantitative PCR kits may comprise instructions for performing the reaction and methods for interpreting and analyzing the data resulting from performing the reaction. In a specific embodiment, the kits contain instructions for predicting whether an inflammatory disease in a patient is clinically sensitive to apremilast.

For antibody-based kits, the kit can comprise, for example: (1) a first antibody (which may or may not be attached to a solid support) that binds to a peptide, polypeptide or protein of interest; and, optionally, (2) a second, different antibody that binds to either the first antibody or the peptide, polypeptide, or protein, and is conjugated to a detectable label (e.g., a fluorescent label, radioactive isotope, or enzyme). In a specific embodiment, the peptide, polypeptide, or protein of interest is associated with or indicative of a condition (e.g., a disease). The antibody-based kits may also comprise beads for conducting immunoprecipitation. Each component of the antibody-based kits is generally in its own suitable container. Thus, these kits generally comprise distinct containers suitable for each antibody and reagent. Further, the antibody-based kits may comprise instructions for performing the assay and methods for interpreting and analyzing the data resulting from performing the assay. In a specific embodiment, the kits contain instructions for predicting whether an inflammatory disease in a patient is clinically sensitive to apremilast.

In some embodiments, the kits provided herein comprise materials for measuring the expression levels of one or more biomarkers selected from the group consisting of Alpha-1-Antitrypsin, Alpha-2-Macroglobulin, Beta-2-Microglobulin, Brain-Derived Neurotrophic Factor, C-Reactive Protein, Complement C3, Eotaxin-1, Factor VII, Ferritin, Fibrinogen, Granulocyte-Macrophage Colony-Stimulating Factor, Haptoglobin, Intercellular Adhesion Molecule 1, Interferon gamma, Interleukin-1 alpha, Interleukin-1 beta, Interleukin-1 receptor antagonist, Interleukin-10, Interleukin-12 Subunit p40, Interleukin-12 Subunit p'70, Interleukin-15, Interleukin-17, Interleukin-2, Interleukin-23, Interleukin-3, Interleukin-4, Interleukin-5, Interleukin-6, Interleukin-7, Interleukin-8, Macrophage Inflammatory Protein-1 alpha, Macrophage Inflammatory Protein-1 beta, Matrix Metalloproteinase-3, Matrix Metalloproteinase-9, MCP1, Stem Cell Factor, T-Cell-Specific Protein RANTES, Tissue Inhibitor of Metalloproteinases, Tumor Necrosis Factor alpha, Tumor Necrosis Factor beta, Tumor necrosis factor receptor 2, Vascular Cell Adhesion Molecule-1, Vascular Endothelial Growth Factor, Vitamin D-Binding Protein, von Willebrand Factor, Osteoprotegerin, Interleukin-18, RANKL, and Sclerostin.

In certain embodiments of the methods and kits provided herein, solid phase supports are used for purifying proteins, labeling samples, or carrying out the solid phase assays. Examples of solid phases suitable for carrying out the methods disclosed herein include beads, particles, colloids, single surfaces, tubes, multi-well plates, microtiter plates, slides, membranes, gels, and electrodes. When the solid phase is a particulate material (e.g., a bead), it is, in one embodiment, distributed in the wells of multi-well plates to allow for parallel processing of the solid phase supports.

It is noted that any combination of the above-listed embodiments, for example, with respect to one or more reagents, such as, without limitation, nucleic acid primers, solid support, and the like, are also contemplated in relation to any of the various methods and/or kits provided herein.

Certain embodiments of the invention are illustrated by the following non-limiting examples.

5. EXAMPLES

Some embodiments are illustrated by the following non-limiting examples. The examples should not be construed as a limitation in the scope thereof.

5.1 Example 1

Unsupervised Clustering Based on Biomarker Expression Profiles Discovered a Patient Group More Likely to be Responsive to Apremilast In this example, a group of ankylosing spondylitis patients was identified based on expression profile of 49 biomarkers as being more likely to be responsive to a treatment with apremilast. In particular, Myriad RBM inflammation MAP biomarker panel (having 49 biomarkers) was used to profile 280 patient samples in the study, among which 255 patient samples produced measurable biomarker levels. In these 255 patient samples, 95 patient samples were treated with 20 mg apremilast ("Apremilast 20 mg Arm Group"). Within the Apremilast 20 mg Arm Group, 36 patient samples were responsive to the treatment and 59 patient samples were not responsive to the treatment. 80 patient samples were treated with 30 mg apremilast ("Apremilast 30 mg Arm Group"). Within Apremilast 30 mg Arm Group, 31 patient samples were responsive to the treatment and 49 patient samples were not responsive to the treatment. The remaining 80 patient samples were control samples (placebo arm).

Unsupervised clustering was then used to analyze the biomarker expression profiles for these patient samples based on the 49 biomarkers (consensus clustering/distance (1-PCor)/Ward linkage method). These 49 biomarkers were Alpha-1-Antitrypsin, Alpha-2-Macroglobulin, Beta-2-Microglobulin, Brain-Derived Neurotrophic Factor, C-Reactive Protein, Complement C3, Eotaxin-1, Factor VII, Ferritin, Fibrinogen, Granulocyte-Macrophage Colony-Stimulating Factor, Haptoglobin, Intercellular Adhesion Molecule 1, Interferon gamma, Interleukin-1 alpha, Interleukin-1 beta, Interleukin-1 receptor antagonist, Interleukin-10, Interleukin-12 Subunit p40, Interleukin-12 Subunit p70, Interleukin-15, Interleukin-17, Interleukin-2, Interleukin-23, Interleukin-3, Interleukin-4, Interleukin-5, Interleukin-6, Interleukin-7, Interleukin-8, Macrophage Inflammatory Protein-1 alpha, Macrophage Inflammatory Protein-1 beta, Matrix Metalloproteinase-3, Matrix Metalloproteinase-9, MCP1, Stem Cell Factor, T-Cell-Specific Protein RANTES, Tissue Inhibitor of Metalloproteinases, Tumor Necrosis Factor alpha, Tumor Necrosis Factor beta, Tumor necrosis factor receptor 2, Vascular Cell Adhesion Molecule-1, Vascular Endothelial Growth Factor, Vitamin D-Binding Protein, von Willebrand Factor, Osteoprotegerin, Interleukin-18, RANKL, and Sclerostin.

The results are shown in the plot of FIG. 1A. As shown, a group of 50 patients (cluster 4) were identified as representing about 30% of the total treatment arm population. For reasons explained in Section 5.2 below, this group of patients is referred to herein as the "MCP1 low patient group." As indicated in FIG. 1B, this cluster of 50 ankylosing spondylitis patients is significantly associated with responsiveness to apremilast. In particular, within this group of 50 patients, the response rate was about 54%, higher than the response rate in the remaining patients which was about 31%.

This group of 50 patients was comprised of 25 patients who received 30 mg apremilast and 25 patients who received 20 mg of apremilast. Looking at the individual treatment arms, the response rate was even more pronounced in the patients receiving 30 mg apremilast. More specifically, 16 out of 25 of the patients receiving 30 mg apremilast treatment responded, which produced a response rate of 64%. This compares to the response rate of the remaining patients in the Apremilast 30 mg Arm Group, which was 27%.

5.2 Example 2

Using Expression Level of a Single Biomarker, such as MCP1, to Differentiate a Patient Group Having Higher Response Rate from the Remaining Patients Univariate comparison of the expression level of each of the 49 biomarkers was performed between cluster 4 patient group and the remaining patients identified and described in Section 5.1 above. Only treatment arm populations were used. The placebo group was excluded. The representative results are shown in Table 1 below.

TABLE 1

Comparison of Individual Biomarker between Cluster 4 and the Rest Patients

| Biomarker | logFC | AveExpr | adj. P. Val |
|---|---|---|---|
| MCP1 | −2.26 | −0.13 | 0.00 |
| von Willebrand Factor | 0.82 | 0.07 | 0.00 |
| Interleukin-8 | −1.13 | 0.05 | 0.00 |
| C-Reactive Protein | 0.67 | −0.19 | 0.00 |
| Alpha-1-Antitrypsin | 0.66 | −0.01 | 0.00 |
| Macrophage Inflammatory Protein-1 beta | −0.76 | 0.09 | 0.00 |
| Interleukin-1 receptor antagonist | 0.53 | −0.19 | 0.00 |
| Eotaxin-1 | −0.36 | −0.09 | 0.00 |
| Interleukin-15 | 0.48 | −0.36 | 0.01 |
| Fibrinogen | 0.96 | −0.12 | 0.01 |
| Vascular Cell Adhesion Molecule-1 | −0.51 | 0.11 | 0.01 |
| Matrix Metalloproteinase-3 | 0.51 | 0.04 | 0.02 |
| Interleukin-18 | −0.41 | 0.01 | 0.04 |
| Sclerostin | −0.43 | −0.02 | 0.04 |
| Complement C3 | 0.38 | −0.14 | 0.04 |
| Haptoglobin | 0.56 | −0.20 | 0.05 |
| Tissue Inhibitor of Metalloproteinases | −0.64 | 0.21 | 0.05 |
| Osteoprotegerin | −0.40 | 0.18 | 0.09 |

In Table 1, a log FC value below 0 indicates a lower expression level of the biomarker in the cluster 4 patient group as compared with the rest patients, and a log FC value above 0 indicates a higher expression level of the biomarker in the cluster 4 patient group as compared with the rest patients.

Each biomarker was then further analyzed for its association with the cluster 4 patient group. MCP1 cytokine was identified as being able to most strongly differentiate the cluster 4 group with the remaining patients. As such, cluster 4 patient group is herein referred to as the "MCP1 low group" or "MCP1 low cluster." As shown in FIG. 2A, the patients that represent MCP1 low group had significantly lower expression level of MCP1 as compared with the rest of the treated patients. The threshold derived from the mid-point (or average) of the median of MCP1 low cluster and the median of non MCP1 low patients was 93.5 pg/ml (see the dash line in the right panel of FIG. 2A).

As shown in FIG. 2B, the level of MCP1 was used to differentiate a small patient subgroup (14% of total population) highly responsive to apremilast (in apremilast arm with either 20 mg or 30 mg apremilast) with a response rate of about 62.5%. Similarly, as shown in FIG. 2C, the level of a single biomarker, MCP1, differentiated a patient subgroup (20% of apremilast 30 mg arm) with a response rate to 30 mg apremilast treatment of about 66.6%. As such, the level of a single biomarker, MCP1, can be used for predicting the patient's response to apremilast treatment.

The performance of using MCP1 expression level alone as a biomarker to predict if a patient belongs to cluster 4 (MCP1 low cluster) was evaluated by cross validation. The data from the samples was split into 10 subsets (10-folds), where each fold had equal size and had a similar proportion of MCP1 low to non-MCP1 low samples. One fold (10% of the data) was held out as a test set, and a classifier was learned from the remainder of the data (the other 90%, also called the training set). The learned model was then applied to the held-out test data to generate predictions of MCP1 low cluster membership for each test sample, which was then compared to the actual labels of cluster membership. This generated an unbiased estimate of how well the classifier would identify members of the MCP1 low cluster in unseen and future data. The process was performed 10 times, holding out a different test fold each time, and training on the remaining 9-folds. Final performance statistics were calculated by aggregating the predictions over all the test folds, resulting in unbiased cluster membership predictions for the entire sample set (all patients).

Furthermore, within each training set in the process above (90% of the data), another round of cross validation was performed, splitting the training set into 10 folds, holding out 1 fold (9% of the data), and training on the remaining 9-folds (81% of the data). The model was trained and tested over all the internal folds using a range of possible model parameters. The optimal parameters were selected as the ones which yielded the best classification performance (as determined by the AUC metrics) over the internal cross validation test folds. Finally, back in the outer loop of cross validation, the model was trained on the whole training set (90% of the data) using only the optimal parameters found in the internal loop. The model was applied to the outer test fold (10% of the data), which was never used in the parameter-setting or model-building process. This process is called nested cross validation. The performance of using MCP1 as a biomarker is shown in Table 2 below.

TABLE 2

Performance of MCP1 as a Biomarker

| NB | acc | auc | mcc | sens | spec | ppv | npv |
|---|---|---|---|---|---|---|---|
| MCP1 | 0.80 | 0.83 | 0.48 | 0.40 | 0.97 | 0.83 | 0.80 |

In Table 2, ACC (accuracy) indicates the proportion of predictions that the classifier gets correct. AUC indicates the area under the curve, given a classification score for each sample. AUC is the probability that a randomly picked positive sample (a sample from MCP1 low cluster) will have a higher score than a randomly picked negative sample (a sample not from MCP1 low cluster), i.e., when compared to known response of the patients whose data points were withheld from model building and subsequently predicted in order to estimate classifier performance (see earlier descriptions of cross-validation). MCC (matthews correlation coefficient) is a correlation coefficient between the observed and predicted classifications. SENS indicates sensitivity or true positive rate, which means the proportion that is correctly classified in all MCP1 low samples. SPEC indicates specificity or true negative rate, which means the proportion that is correctly classified in all non-MCP1 low samples. PPV indicates positive predictive value, which means the proportion that is correctly classified out of all people predicted to be in MCP1 low group. NPV indicates negative predictive value, which means the proportion that is correctly classified out of all people predicted to be not in MCP1 low group.

5.2.1 Determination of a Threshold Level of MCP1

A threshold level of MCP1 (or another biomarker) can be calculated using various methods. Three methods for calculating a threshold level of MCP1 were exemplified in this study. FIG. 2D shows MCP1 distribution using a threshold level (103.97 pg/ml) calculated based on the median value of the total population in this study.

When the threshold was calculated as the mid-point between median MCP1 level in cluster 4 patient group and median MCP1 level in the remaining patients, the threshold level was 93.5 pg/ml. The distribution of MCP1 using this threshold level is shown in FIG. 2E. Using the threshold level of 93.5 pg/ml in the apremilast arms (both 20 mg and 30 mg arms), 36% of the patients that received a treatment with apremilast were grouped into MCP1 low group, and the MCP1 low group had a response rate of 49%. Looking at just the apremilast 30 mg arm and using the same threshold level of 93.5 pg/ml, 45% of the patients that received 30 mg apremilast treatment were classified into the MCP1 low group, and these patients had a response rate of 56%.

A third method used to calculate a MCP1 threshold level was by calculating the mean of thresholds obtained from 10-fold cross validation (discussed above). In particular, each fold provided an optimal threshold according to the AUC metric when classifying for cluster membership. Then, the mean value of the 10 thresholds was calculated. Using this method, the threshold of MCP1 was calculated as 75.63 pg/ml. The distribution of MCP1 based on this threshold level is shown in FIG. 2F. With this more restrictive learned threshold, the population selected into the MCP1 low group decreased while the response rate of the MCP1 low subgroup increased. For example, in the apremilast 30 mg arm, 22% of the patients that received 30 mg apremilast treatment were classified into the MCP1 low group, and these patients had a higher response rate of 67%.

Similar evaluation was also applied to each of the other biomarkers. Top biomarkers selected by nested cross validation are listed (in order) in Table 3.

TABLE 3

Top Biomarkers Selected by Nested Cross Validation

| Rank | Top Features | 2 | 3 | 4 | 5 | 6 | 7 | 8 | 9 | 10 |
|---|---|---|---|---|---|---|---|---|---|---|
| 1 | MCP1 | 8 | 10 | 10 | 10 | 10 | 10 | 10 | 10 | 10 |
| 2 | Interleukin-15 | 5 | 7 | 7 | 7 | 10 | 10 | 10 | 10 | 10 |
| 3 | C-Reactive Protein | 1 | 5 | 6 | 7 | 8 | 9 | 9 | 10 | 10 |
| 4 | Matrix Metalloproteinase-3 | 1 | 2 | 4 | 6 | 6 | 8 | 10 | 10 | 10 |
| 5 | Interleukin-1 receptor antagonist | 1 | 1 | 3 | 4 | 6 | 7 | 7 | 8 | 9 |
| 6 | von Willebrand Factor | 0 | 0 | 1 | 4 | 4 | 6 | 7 | 8 | 9 |
| 7 | Eotaxin-1 | 2 | 3 | 5 | 7 | 7 | 7 | 7 | 8 | 8 |
| 8 | Alpha-1-Antitrypsin | 0 | 0 | 1 | 2 | 3 | 3 | 3 | 4 | 8 |
| 9 | Macrophage Inflammatory Protein-1 beta | 1 | 1 | 2 | 2 | 3 | 4 | 5 | 6 | 7 |
| 10 | Vascular Cell Adhesion Molecule-1 | 0 | 0 | 0 | 0 | 1 | 3 | 6 | 7 | 7 |
| 11 | Tissue Inhibitor of Metalloproteinases | 1 | 1 | 1 | 1 | 1 | 2 | 2 | 2 | 2 |
| 12 | Osteoprotegerin | 0 | 0 | 0 | 0 | 0 | 0 | 0 | 2 | 2 |
| 13 | Vascular Endothelial Growth Factor | 0 | 0 | 0 | 0 | 0 | 0 | 2 | 2 | 2 |
| 14 | Alpha-2-Macroglobulin | 0 | 0 | 0 | 0 | 0 | 0 | 1 | 1 | 1 |
| 15 | Brain-Derived Neurotrophic Factor | 0 | 0 | 0 | 0 | 0 | 0 | 0 | 1 | 1 |
| 16 | Intercellular Adhesion Molecule 1 | 0 | 0 | 0 | 0 | 0 | 0 | 0 | 0 | 1 |
| 17 | Interleukin-18 | 0 | 0 | 0 | 0 | 1 | 1 | 1 | 1 | 1 |
| 18 | Matrix Metalloproteinase-9 | 0 | 0 | 0 | 0 | 0 | 0 | 0 | 0 | 1 |
| 19 | Vitamin D-Binding Protein | 0 | 0 | 0 | 0 | 0 | 0 | 0 | 0 | 1 |

Each of these top ranked biomarkers may be used alone to classify a patient for predicting the patient's response to a treatment with apremilast.

5.3 Example 3

Using Expression Levels of Multiple Biomarkers to Differentiate a Patient Group Having Higher Response Rate from the Remaining Patients The performance of using multiple biomarkers to separate a patent group with higher response rate was studied in this example. Two classifiers—Naive Bayes and Weighted RSVM—were exemplified to classify a patient based on multiple biomarker levels.

Naive Bayes learns a probabilistic model between features and cluster membership that maximizes the posterior probability of the observed subgroups given the features (assuming independence of all features). Formula of Naive Bayes is:

$$\hat{y} = \underset{k \in \{1,\ldots,K\}}{\operatorname{argmax}} p(C_k) \prod_{i=1}^{n} p(x_i | C_k),$$

where p(Ck) represents overall class (MCP1 low cluster membership) probability, K is number of classes (here two), n is the number of features (number of biomarkers used, e.g., 2 for Top 2), x are the features themselves and p(xi|Ck) is the posterior probability of observing $x_i$ given class $C_k$.

SVM (support vector machine) is a classifier that draws a boundary between MCP1 low and non-MCP1low clusters. SVMs are supervised learning models with associated learning algorithms that analyze data and recognize patterns, used for classification and regression analysis. Given a set of training examples, each marked for belonging to one of two categories, an SVM training algorithm builds a model that assigns new examples into one category or the other, making it a non-probabilistic binary linear classifier. An SVM model is a representation of the examples as points in space, mapped so that the examples of the separate categories are divided by a clear gap that is as wide as possible. New examples are then mapped into that same space and predicted to belong to a category based on which side of the gap they fall on. Weighted RSVM is weighted reduced SVM. Reduced version of SVM uses a subset of the data to improve efficiency and generalization of the model. Weighted version balances classes of different sizes. Formula of SVM is $$f(\vec{x}) = \operatorname{sign}(\Sigma a_j y_j K(\vec{x}_j, \vec{x}) + b)$$

where $x_i$ is a sample represented by a vector of features and x is all the samples, K is a kernel matrix which encodes the distance between all samples, $y_i$ is the cluster membership for sample i, alpha is an indicator variable that describes which samples are closest to the classification boundary and b is an offset.

The performance of these two classifiers for classifying patients using top 2-10 or all 49 biomarkers are shown in FIG. 3A, and summarized in Tables 4-5 below.

TABLE 4

Performance of Naive Bayes for MCP1 Low Membership Prediction

| NB | acc | auc | mcc | sens | spec | ppv | npv |
|---|---|---|---|---|---|---|---|
| top 2 | 0.82 | 0.87 | 0.52 | 0.46 | 0.96 | 0.82 | 0.82 |
| top 3 | 0.83 | 0.91 | 0.57 | 0.48 | 0.98 | 0.89 | 0.82 |
| top 4 | 0.84 | 0.90 | 0.60 | 0.62 | 0.94 | 0.79 | 0.86 |
| top 5 | 0.86 | 0.91 | 0.63 | 0.64 | 0.94 | 0.82 | 0.87 |
| top 6 | 0.84 | 0.90 | 0.61 | 0.66 | 0.92 | 0.77 | 0.87 |
| top 7 | 0.84 | 0.92 | 0.61 | 0.70 | 0.90 | 0.74 | 0.88 |
| top 8 | 0.87 | 0.93 | 0.67 | 0.74 | 0.92 | 0.79 | 0.90 |
| top 9 | 0.90 | 0.94 | 0.74 | 0.78 | 0.94 | 0.85 | 0.91 |
| top 10 | 0.91 | 0.95 | 0.77 | 0.82 | 0.94 | 0.85 | 0.93 |
| All | 0.79 | 0.89 | 0.54 | 0.78 | 0.80 | 0.61 | 0.90 |

TABLE 5

Performance of Weighted RSVM for MCP1 Low Membership Prediction

| WRSVM | acc | auc | mcc | sens | spec | ppv | npv |
|---|---|---|---|---|---|---|---|
| top1 (MCP1) | 0.82 | 0.74 | 0.53 | 0.5 | 0.95 | 0.81 | 0.83 |
| top 2 | 0.79 | 0.82 | 0.49 | 0.66 | 0.84 | 0.62 | 0.86 |
| top 3 | 0.84 | 0.89 | 0.61 | 0.70 | 0.90 | 0.74 | 0.88 |
| top 4 | 0.84 | 0.91 | 0.60 | 0.70 | 0.90 | 0.73 | 0.88 |
| top 5 | 0.86 | 0.91 | 0.65 | 0.74 | 0.90 | 0.76 | 0.90 |
| top 6 | 0.88 | 0.93 | 0.70 | 0.76 | 0.93 | 0.81 | 0.91 |
| top 7 | 0.87 | 0.94 | 0.68 | 0.80 | 0.90 | 0.75 | 0.92 |
| top 8 | 0.90 | 0.95 | 0.76 | 0.80 | 0.94 | 0.85 | 0.92 |
| top 9 | 0.89 | 0.97 | 0.74 | 0.84 | 0.91 | 0.79 | 0.93 |
| top 10 | 0.90 | 0.97 | 0.77 | 0.86 | 0.92 | 0.81 | 0.94 |
| All | 0.94 | 0.98 | 0.85 | 0.90 | 0.95 | 0.88 | 0.96 |

As discussed above, ACC indicates the proportion of predictions that the classifier gets correct. AUC indicates the probability that a randomly picked positive sample will have a higher score than a randomly picked negative sample. MCC is a correlation coefficient between the observed and predicted classifications. SENS indicates sensitivity or true positive rate, which means the proportion that is correctly classified in all MCP1 low samples. SPEC indicates specificity or true negative rate, which means the proportion that is correctly classified in all non-MCP1 low samples. PPV indicates positive predictive value, which means the proportion that is correctly classified out of all people predicted to be in MCP1 low group. NPV indicates negative predictive value, which means the proportion that is correctly classified out of all people predicted to be not in MCP1 low group.

As shown in FIG. 3A and Tables 4-5, performance improved as the number of biomarkers increased. For example, the sensitivity increased with the number of biomarkers for both classifiers.

Identification of a patient group with higher response rate using top 2 biomarkers (MCP1 and Interleukin-15) is shown in FIG. 3B. Identification of a patient group with higher response rate using top 5 biomarkers (MCP1, Interleukin-15, C-Reactive Protein, Matrix Metalloproteinase-3, and Interleukin-1 receptor antagonist) is shown in FIG. 3C. Identification of a patient group with higher response rate using top 10 biomarkers (MCP1, Interleukin-15, C-Reactive Protein, Matrix Metalloproteinase-3, Interleukin-1 receptor antagonist, von Willebrand Factor, Eotaxin-1, Alpha-1-Antitrypsin, Macrophage Inflammatory Protein-1 beta, and Vascular Cell Adhesion Molecule-1) is shown in FIG. 3D. Identification of a patient group with higher response rate using all 49 biomarkers is shown in FIG. 3E. The response rate for each case is indicated in these figures.

These results indicate that the expression profile of these 49 biomarkers, or a subset thereof (e.g., top 2, top 3, top 4, top 5, top 5, top 6, top 7, top 8, top 9, or top 10 biomarkers identified in the present study) can be used to classify a patient for the purpose of predicting the patient's response to apremilast treatment.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed is:

1. A method of identifying a subject having ankylosing spondylitis who is likely to be responsive to a treatment with apremilast, predicting the responsiveness of a subject having or suspected of having ankylosing spondylitis to a treatment with apremilast, or treating a subject having ankylosing spondylitis, comprising:
   (a) identifying the subject having ankylosing spondylitis that may be responsive to a treatment with apremilast, comprising:
      i. obtaining a sample from the subject;
      ii. measuring the level of MCP1 in the sample; and
      iii. diagnosing the subject as being likely to be responsive to apremilast if the level of MCP1 in the sample is lower than a threshold level of MCP1, and
   (b) administering the subject a therapeutically effective amount of apremilast if the subject is identified as being likely to be responsive to treatment with apremilast.

2. The method of claim 1, wherein the threshold level of MCP1 is determined based on the levels of MCP1 in a population.

3. The method of claim 1, wherein the threshold level of MCP1 selected from the group consisting of between 200 pg/ml to 50 pg/ml and between 105 pg/ml to 70 pg/ml.

4. The method of claim 1, wherein the threshold level of MCP1 is lower than 200 pg/ml, 150 pg/ml, 120 pg/ml, 105 pg/ml, 100 pg/ml, 95 pg/ml, 90 pg/ml, 85 pg/ml, 80 pg/ml, 75 pg/ml, or 70 pg/ml.

5. The method of claim 1, wherein the threshold level of MCP1 is about 105 pg/ml.

6. The method of claim 1, wherein the threshold level of MCP1 is about 95 pg/ml.

7. The method of claim 1, wherein the threshold level of MCP1 is about 75 pg/ml.

8. The method of claim 1, wherein the subject is diagnosed as having more than a 50% to 90% likelihood of being responsive to apremilast if the level of MCP1 is lower than the threshold level of MCP1.

9. The method of claim 1, wherein the subject is diagnosed as having more than a 50%, 60%, 70%, 80% or 90% likelihood of being responsive to apremilast if the level of MCP1 is lower than the threshold level of MCP1.

10. The method of claim 1, wherein the method further comprises measuring the level of one or more additional biomarkers selected from the group consisting of Alpha-1-Antitrypsin, Alpha-2-Macroglobulin, Beta-2-Microglobulin, Brain-Derived Neurotrophic Factor, C-Reactive Protein, Complement C3, Eotaxin-1, Factor VII, Ferritin, Fibrinogen, Granulocyte-Macrophage Colony-Stimulating Factor, Haptoglobin, Intercellular Adhesion Molecule 1, Interferon gamma, Interleukin-1 alpha, Interleukin-1 beta, Interleukin-1 receptor antagonist, Interleukin-10, Interleukin-12 Subunit p40, Interleukin-12 Subunit p70, Interleukin-15, Interleukin-17, Interleukin-2, Interleukin-23, Interleukin-3, Interleukin-4, Interleukin-5, Interleukin-6, Interleukin-7, Interleukin-8, Macrophage Inflammatory Protein-1 alpha, Macrophage Inflammatory Protein-1 beta, Matrix Metalloproteinase-3, Matrix Metalloproteinase-9, Stem Cell Factor, T-Cell-Specific Protein RANTES, Tissue Inhibitor of Metalloproteinases, Tumor Necrosis Factor alpha, Tumor Necrosis Factor beta, Tumor necrosis factor receptor 2, Vascular Cell Adhesion Molecule-1, Vascular Endothelial Growth Factor, Vitamin D-Binding Protein, von Willebrand Factor, Osteoprotegerin, Interleukin-18, RANKL, and Sclerostin.

11. The method of claim 1, wherein the method further comprises measuring the level of one additional biomarker Interleukin-15.

12. The method of claim 1, wherein the method further comprises measuring the level of two additional biomarkers including Interleukin-15 and C-Reactive Protein.

13. The method of claim 1, wherein the method further comprises measuring the level of three additional biomarkers including Interleukin-15, C-Reactive Protein, and Matrix Metalloproteinase-3.

14. The method of claim 1, wherein the method further comprises measuring the level of four additional biomarkers including Interleukin-15, C-Reactive Protein, Matrix Metalloproteinase-3, and Interleukin-1 receptor antagonist.

15. The method of claim 1, wherein the method further comprises measuring the level of five additional biomarkers including Interleukin-15, C-Reactive Protein, Matrix Metalloproteinase-3, Interleukin-1 receptor antagonist, and von Willebrand Factor.

16. The method of claim 1, wherein the method further comprises measuring the level of six additional biomarkers including Interleukin-15, C-Reactive Protein, Matrix Metalloproteinase-3, Interleukin-1 receptor antagonist, von Willebrand Factor, and Eotaxin-1.

17. The method of claim 1, wherein the method further comprises measuring the level of seven additional biomarkers including Interleukin-15, C-Reactive Protein, Matrix Metalloproteinase-3, Interleukin-1 receptor antagonist, von Willebrand Factor, Eotaxin-1, and Alpha-1-Antitrypsin.

18. The method of claim 1, wherein the method further comprises measuring the level of eight additional biomarkers including Interleukin-15, C-Reactive Protein, Matrix Metalloproteinase-3, Interleukin-1 receptor antagonist, von Willebrand Factor, Eotaxin-1, Alpha-1-Antitrypsin, and Macrophage Inflammatory Protein-1 beta.

19. The method of claim 1, wherein the method further comprises measuring the level of nine additional biomarkers including Interleukin-15, C-Reactive Protein, Matrix Metalloproteinase-3, Interleukin-1 receptor antagonist, von Willebrand Factor, Eotaxin-1, Alpha-1-Antitrypsin, Macrophage Inflammatory Protein-1 beta, and Vascular Cell Adhesion Molecule-1.

* * * * *